United States Patent [19]

Fisher et al.

[11] Patent Number: 5,705,515
[45] Date of Patent: Jan. 6, 1998

[54] SUBSTITUTED SULFONAMIDES AS SELECTIVE β-3 AGONISTS FOR THE TREATMENT OF DIABETES AND OBESITY

[75] Inventors: Michael H. Fisher, Ringoes; Elizabeth M. Naylor, Scotch Plains; Emma R. Parmee, Hoboken; Thomas Shih; Hyun Ok, both of Edison; Ann E. Weber, Scotch Plains, all of N.J.

[73] Assignee: Merck & Co., Inc., Rahway, N.J.

[21] Appl. No.: 684,901

[22] Filed: Jul. 25, 1996

Related U.S. Application Data

[63] Continuation-in-part of Ser. No. 445,630, May 22, 1995, Pat. No. 5,561,142, which is a continuation-in-part of Ser. No. 404,565, Mar. 21, 1995, abandoned, which is a continuation-in-part of Ser. No. 233,166, Apr. 26, 1994, abandoned.

[51] Int. Cl.$^6$ .............. A61K 31/425; A61K 31/40; C07D 277/02; C07D 275/02
[52] U.S. Cl. .............. 514/365; 514/378; 514/300; 514/302; 514/415; 548/205; 548/247; 548/491; 548/469; 546/112; 546/115
[58] Field of Search .............. 546/112, 115; 548/205, 247, 469, 491; 514/300, 302, 365, 378, 415

[56] References Cited

U.S. PATENT DOCUMENTS

| | | | |
|---|---|---|---|
| 3,452,037 | 6/1969 | Santilli et al. | 514/365 |
| 3,816,516 | 6/1974 | Cox et al. | 514/653 |
| 4,000,193 | 12/1976 | Lunts et al. | 546/344 |
| 4,396,627 | 8/1983 | Ainsworth et al. | 424/285 |
| 4,478,849 | 10/1984 | Ainsworth et al. | 424/285 |
| 4,999,377 | 3/1991 | Caulkett et al. | 424/285 |
| 5,017,619 | 5/1991 | Alig et al. | 514/653 |
| 5,153,210 | 10/1992 | Ainsworth et al. | 546/344 |
| 5,321,036 | 6/1994 | Sher | 514/366 |

FOREIGN PATENT DOCUMENTS

| | | |
|---|---|---|
| 0091749 | 10/1983 | European Pat. Off. . |
| 0427480 | 5/1991 | European Pat. Off. . |
| 0455006 | 11/1991 | European Pat. Off. . |
| 0068669 | 1/1993 | European Pat. Off. . |
| 0611003 | 8/1994 | European Pat. Off. . |
| 1.1-9.588 | 3/1968 | United Kingdom . |
| 1565080 | 4/1990 | United Kingdom . |

*Primary Examiner*—Zinna Northington Davis
*Attorney, Agent, or Firm*—Mollie M. Yang; David L. Rose

[57] ABSTRACT

Substituted sulfonamides are selective $\beta_3$ adrenergic receptor agonists with very little $\beta_1$ and $\beta_2$ adrenergic receptor activity and as such the compounds are capable of increasing lipolysis and energy expenditure in cells. The compounds thus have potent activity in the treatment of Type II diabetes and obesity. The compounds can also be used to lower triglyceride levels and cholesterol levels or raise high density lipoprotein levels or to decrease gut motility. In addition, the compounds can be used to reduced neurogenic inflammation or as antidepressant agents. The compounds are prepared by coupling an aminoalkylphenyl-sulfonamide with an appropriately substituted epoxide. Compositions and methods for the use of the compounds in the treatment of diabetes and obesity and for lowering triglyceride levels and cholesterol levels or raising high density lipoprotein levels or for increasing gut motility are also disclosed.

13 Claims, No Drawings

SUBSTITUTED SULFONAMIDES AS SELECTIVE β-3 AGONISTS FOR THE TREATMENT OF DIABETES AND OBESITY

CROSS REFERENCE

This is a continuation-in-part of application U.S. Ser. No. 08/445,630 filed May 22, 1995, now U.S. Pat. No. 5,561,142, which is a continuation-in-part of U.S. Ser. No. 08/404,565 filed Mar. 21, 1995, now abandoned, which is a continuation-in-part of U.S. Ser. No. 08/233,166 filed Apr. 26, 1994, now abandoned; these applications are hereby incorporated by reference in their entirety.

BACKGROUND OF THE INVENTION

β-Adrenoceptors have been subclassified as $\beta_1$ and $\beta_2$ since 1967. Increased heart rate is the primary consequence of $\beta_1$-receptor stimulation, while bronchodilation and smooth muscle relaxation typically result from $\beta_2$ stimulation. Adipocyte lipolysis was initially thought to be solely a $\beta_1$-mediated process. However, more recent results indicate that the receptor-mediating lipolysis is atypical in nature. These atypical receptors, later called $\beta_3$-adrenoceptors, are found on the cell surface of both white and brown adipocytes where their stimulation promotes both lipolysis (breakdown of fat) and energy expenditure.

Early developments in this area produced compounds with greater agonist activity for the stimulation of lipolysis ($\beta_3$ activity) than for stimulation of atrial rate ($\beta_1$) and tracheal relaxation ($\beta_2$). These early developments disclosed in Ainsworth et al., U.S. Pat. Nos. 4,478,849 and 4,396,627, were derivatives of phenylethanolamines.

Such selectivity for $\beta_3$-adrenoceptors could make compounds of this type potentially useful as antiobesity agents. In addition, these compounds have been reported to show antihyperglycemic effects in animal models of non-insulin-dependent diabetes mellitus.

A major drawback in treatment of chronic diseases with $\beta_3$ agonists is the potential for stimulation of other β-receptors and subsequent side effects. The most likely of these include muscle tremor ($\beta_2$) and increased heart rate ($\beta_1$). Although these phenylethanolamine derivatives do possess some $\beta_3$ selectivity, side effects of this type have been observed in human volunteers. It is reasonable to expect that these side effects resulted from partial $\beta_1$ and/or $\beta_2$ agonism.

More recent developments in this area are disclosed in Ainsworth et al., U.S. Pat. No. 5,153,210, Caulkett et al., U.S. Pat. No. 4,999,377, Alig et al., U.S. Pat. No. 5,017,619, Lecount et al., European Patent 427480 and Bloom et al., European Patent 455006.

Even though these more recent developments purport to describe compounds with greater $\beta_3$ selectivity over the $\beta_1$ and $\beta_2$ activities, this selectivity was determined using rodents, in particular, rats as the test animal. Because even the most highly selective compounds, as determined by these assays, still show signs of side effects due to residual $\beta_1$ and $\beta_2$ agonist activity when the compounds are tested in humans, it has become apparent that the rodent is not a good model for predicting human $\beta_3$ selectivity.

Recently, assays have been developed which more accurately predict the effects that can be expected in humans. These assays utilize cloned human $\beta_3$ receptors which have been expressed in Chinese hamster ovary cells. See Emorine et al, *Science*, 1989, 245:1118–1121; and Liggett, *Mol. Pharmacol.*, 1992, 42:634–637. The agonist and antagonist effects of the various compounds on the cultivated cells provide an indication of the antiobesity and antidiabetic effects of the compounds in humans.

SUMMARY OF THE INVENTION

The instant invention is concerned with substituted sulfonamides which are useful as antiobesity and antidiabetic compounds. Thus, it is an object of this invention to describe such compounds. It is a further object to describe the specific preferred stereoisomers of the substituted sulfonamides. A still further object is to describe processes for the preparation of such compounds. Another object is to describe methods and compositions which use the compounds as the active ingredient thereof. Further objects will become apparent from reading the following description.

DESCRIPTION OF THE INVENTION

The present invention provides compounds having the formula I:

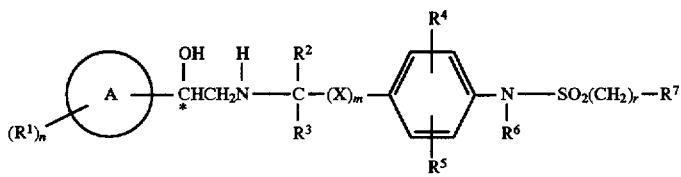

where
n is 0 to 5;
m is 0 or 1;
r is 0 to 3;
A is
  (1) a 5 or 6-membered heterocyclic ring with from 1 to 4 heteroatoms selected from oxygen, sulfur and nitrogen, excluding pyridinyl,
  (2) a benzene ring fused to a 5 or 6-membered heterocyclic ring with from 1 to 4 heteroatoms selected from oxygen, sulfur and nitrogen, or
  (3) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen;
$R^1$ is
  (1) hydroxy,
  (2) oxo,
  (3) halogen,
  (4) cyano,
  (5) $NR^8R^8$,
  (6) $SR^8$,
  (7) trifluoromethyl,
  (8) $C_1$–$C_{10}$ alkyl,
  (9) $OR^8$,

(10) $S(O)_tR^9$, where t is 1 or 2,
(11) $OCOR^9$,
(12) $NR^8COR^9$,
(13) $COR^9$,
(14) $NR^8SO_2R^9$,
(15) $NR^8CO_2R^8$, or
(16) $C_1-C_{10}$ alkyl substituted by hydroxy, halogen, cyano, $NR^8R^8$, $SR^8$, trifluoromethyl, $OR^8$, $C_3-C_8$ cycloalkyl, phenyl, $NR^8COR^9$, $COR^9$, $S(O)_tR^9$, where t is 1 or 2, $OCOR^9$, $NR^8SO_2R^9$ or $NR^8CO_2R^8$;

$R^2$ and $R^3$ are independently
(1) hydrogen,
(2) $C_1-C_{10}$ alkyl or
(3) $C_1-C_{10}$ alkyl with 1 to 5 substituents selected from hydroxy, $C_1-C_{10}$ alkoxy, and halogen;

X is
(1) —$CH_2$—,
(2) —$CH_2$—$CH_2$—,
(3) —CH=CH— or
(4) —$CH_2O$—;

$R^4$ and $R^5$ are independently
(1) hydrogen,
(2) $C_1-C_{10}$ alkyl,
(3) halogen,
(4) $NHR^8$,
(5) $OR^8$,
(6) $S(O)_tR^9$, where t is 1 or 2, or
(7) $NHSO_2R^9$;

$R^6$ is
(1) hydrogen or
(2) $C_1-C_{10}$ alkyl;

$R^7$ is $Z$—$(R^{1a})_n$;

$R^{1a}$ is
(1) $R^1$, with the proviso that when A is phenyl, $R^{1a}$ is not $C_1-C_{10}$ alkyl,
(2) $C_3-C_8$ cycloalkyl,
(3) phenyl optionally substituted with up to 4 groups independently selected from $R^8$, $NR^8R^8$, $OR^8$, $S(O)_tR^8$ where t is 0 to 2, and halogen, or
(4) 5 or 6-membered heterocycle with from 1 to 4 heteroatoms selected from oxygen, sulfur and nitrogen, optionally substituted with up to four groups independently selected from oxo, $R^8$, $NR^8R^8$, $OR^8$, $S(O)_tR^8$ where t is 0 to 2, and halogen;

Z is
(1) phenyl,
(2) naphthyl,
(3) a 5 or 6-membered heterocyclic ring with from 1 to 4 heteroatoms selected from oxygen, sulfur and nitrogen,
(4) a benzene ring fused to a $C_5-C_{10}$ carbocyclic ring,
(5) a benzene ring fused to a 5 or 6-membered heterocyclic ring with from 1 to 4 heteroatoms selected from oxygen, sulfur and nitrogen,
(6) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen, or
(7) a 5 or 6-membered heterocyclic ring with from 1 to 4 heteroatoms selected from oxygen, sulfur and nitrogen fused to a $C_3-C_8$ cycloalkyl ring;

$R^8$ is
(1) hydrogen,
(2) $C_1-C_{10}$ alkyl,
(3) $C_3-C_8$ cycloalkyl,
(4) Z optionally having 1 to 5 substituents selected from halogen, nitro, oxo, $NR^{10}R^{10}$, $C_1-C_{10}$ alkyl, $C_1-C_{10}$ alkoxy, $C_1-C_{10}$ alkylthio, and $C_1-C_{10}$ alkyl having 1 to 5 substituents selected from hydroxy, halogen, $CO_2H$, $CO_2$—$C_1-C_{10}$ alkyl, $SO_2$—$C_1-C_{10}$ alkyl, $C_3-C_8$ cycloalkyl, $C_1-C_{10}$ alkoxy, and Z optionally substituted by from 1 to 3 of halogen, $C_1-C_{10}$ alkyl or $C_1-C_{10}$ alkoxy, or
(5) $C_1-C_{10}$ alkyl having 1 to 5 substituents selected from hydroxy, halogen, $CO_2H$, $CO_2$—$C_1-C_{10}$ alkyl, $SO_2$—$C_1-C_{10}$ alkyl, $C_3-C_8$ cycloalkyl, $C_1-C_{10}$ alkoxy, $C_1-C_{10}$ alkyl, and Z optionally substituted by from 1 to 5 of halogen, trifluoromethyl, trifluoromethoxy, $C_1-C_{10}$ alkyl or $C_1-C_{10}$ alkoxy;

$R^9$ is
(1) $R^8$ or
(2) $NR^8R^8$;

$R^{10}$ is
(1) $C_1-C_{10}$ alkyl, or
(2) two R 10 groups together with the N to which they are attached formed a 5 or 6-membered ring optionally substituted with $C_1-C_{10}$ alkyl; or a pharmaceutically acceptable salt thereof.

In one embodiment of the instant invention A is a 5 or 6-membered heterocyclic ring with from 1 to 4 heteroatoms selected from oxygen, sulfur and nitrogen, excluding pyridyl; a benzene ring fused to a 5 or 6-membered heterocyclic ring with from 1 to 4 heteroatoms selected from oxygen, sulfur and nitrogen; or a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen.

Preferred compounds of the instant invention are realized when in the above structural formula I:

$R^2$ and $R^3$ are hydrogen or methyl;

X is —$CH_2$—;

n is 0 to 3;

m is 1;

r is 0 to 2; and $R^4$, $R^5$ and $R^6$ are hydrogen.

Other preferred compounds of the instant invention are realized when in the above structural formula I:

A is
(1) a 5-membered heterocyclic ring with 1 or 2 heteroatoms selected from nitrogen, oxygen, and sulfur,
(2) a benzene ring fused to a 5-membered heterocyclic ring with 1 or 2 heteroatom selected from oxygen, sulfur and nitrogen, or
(3) a 5- or 6-membered heterocyclic ring with 1 or 2 heteroatoms selected from oxygen, sulfur and nitrogen fused to a 5- or 6-membered heterocyclic ring with 1 or 2 heteroatoms selected from oxygen, sulfur and nitrogen;

$R^1$ is hydroxy, halogen, cyano, trifluoromethyl, $NR^8R^8$, $NR^8SO_2R^9$, $NR^8COR^9$, $NR^8CO_2R^8$, $C_1-C_6$ alkyl optionally substituted by hydroxy; and r is 0 or 2.

More preferred compounds of formula I are those wherein

A is selected from the group consisting of thiazolyl, isoxazolyl, indolinyl, indolyl, furopyridyl, tetrahydrofuropyridyl, 7-azaindolyl and 7-azaindolinyl;

n is 0 to 3;

m is 1;

r is 0;

$R^2$, $R^3$ are each hydrogen;

$R^{1a}$ is
  (1) halogen,
  (2) $NR^8COR^9$, or
  (3) a 5 or 6-membered heterocycle with from 1 to 4 heteroatoms selected from oxygen, sulfur and nitrogen, optionally substituted with up to four groups independently selected from oxo and $R^8$;

Z is phenyl or indolinyl

X is —$CH_2$—.

Representative antiobesity and antidiabetic compounds of the present invention include the following:

N-[4-[2-[[2-Hydroxy-2-(thiazol-5-yl)ethyl]amino]ethyl] phenyl]-4-(3-octyl-2-imidazolidinon-1-yl) benzenesulfonamide;

N-[4-[2-[[2-Hydroxy-2-(thiazol-5-yl)ethyl]amino]ethyl] phenyl]-4-(hexylaminocarbonylamino) benzenesulfonamide;

N-[4-[2-[[2-Hydroxy-2-(thiazol-5-yl)ethyl]amino]ethyl] phenyl]-4-(4-iodo)benzenesulfonamide;

N-[4-[2-[[2-Hydroxy-2-(3-methylisoxazol-5-yl)ethyl] amino]ethyl]phenyl]-1-(4-octylthiazol-2-yl)-5-indolinesulfonamide;

N-[4-[2-[[2-Hydroxy-2-(3-methylisoxazol-5-yl)ethyl] amino]ethyl]phenyl]-4-[5-(3,4-difluorophenylmethyl)-[1,2,4]-oxadiazol-3-yl]benzenesulfonamide;

N-[4-[2-[[2-Hydroxy-2-(3-methylisoxazol-5-yl)ethyl] amino]ethyl]phenyl]-4-(hexylaminocarbonylamino) benzenesulfonamide;

N-[4-[2-[[2-Hydroxy-2-(3-methylisoxazol-5-yl)ethyl] amino]ethyl]phenyl]-4-(3-octyl-2-imidazolidinon-1-yl) benzenesulfonamide;

N-[4-[2-[[2-Hydroxy-2-(3-methylisoxazol-5-yl)ethyl] amino]ethyl]phenyl]-4-[4-(3-cyclopentylpropyl)-5-tetrazolon-1-yl]benzenesulfonamide;

N-[4-[2-[[2-Hydroxy-2-(3-methylisoxazol-5-yl)ethyl] amino]ethyl]phenyl]-4-(4-octyl-5-tetrazolon-1-yl) benzenesulfonamide;

N-[4-[2-[[2-Hydroxy-2-(3-methylisoxazol-5-yl)ethyl] amino]ethyl]phenyl]-4-[5-(3,4,5-trifluorobenzyl)-[1,2,4]-oxadiazol-3-yl]benzenesulfonamide;

N-[4-[2-[[2-Hydroxy-2-(3-methylisoxazol-5-yl)ethyl] amino]ethyl]phenyl]-4-[5-[1-(4-fluorophenyl)-1-methoxymethyl]-[1,2,4]-oxadiazol-3-yl] benzenesulfonamide;

N-[4-[2-[[2-Hydroxy-2-(3-methylisoxyl-5-yl)ethyl]amino] ethyl]phenyl]-1-(6-hexylpyrid-2-yl)-5-indolinesulfonamide;

N-[4-[2-[[2-Hydroxy-2-(3-methylisoxazol-5-yl)ethyl] amino]ethyl]phenyl]-1-[6-(3-cyclopentylpropyl)pyrid-2-yl]-5-indolinesulfonamide;

N-[4-[2-[[2-Hydroxy-2-(3-methylisoxazol-5-yl)ethyl] amino]ethyl]phenyl]-1-(6-octylpyrid-2-yl)-5-indolinesulfonamide;

N-[4-[2-[[2-Hydroxy-2-(3-methylisoxazol-5-yl)ethyl] amino]ethyl]phenyl]4-(5-pentyl-[1,2,4]-oxadiazol-3-yl) benzenesulfonamide;

N-[4-[2-[[2-Hydroxy-2-(3-methylisoxazol-5-yl)ethyl] amino]ethyl]phenyl]4-(5-heptyl-[1,2,4]-oxadiazol-3-yl) benzenesulfonamide;

N-[4-[2-[[2-Hydroxy-2-(5-indolinyl)ethyl]amino]ethyl] phenyl]-1-(4-octylthiazol-2-yl)-5-indolinesulfonamide;

N-[4-[2-[[2-Hydroxy-2-(5-indolyl)ethyl]amino]ethyl] phenyl]-1-(4-octylthiazol-2-yl)-5-indolinesulfonamide;

N-[4-[2-[[2-Hydroxy-2-(5-indolinyl)ethyl]amino]ethyl] phenyl]-4-(5-pentyl-[1,2,4]-oxadiazol-3-yl) benzenesulfonamide;

N-[4-[2-[[2-Hydroxy-2-(5-indolyl)ethyl]amino]ethyl] phenyl]-4-(5-pentyl-[1,2,4]-oxadiazol-3-yl) benzenesulfonamide;

N-[4-[2-[[2-Hydroxy-2-(5-indolyl)ethyl]amino]ethyl] phenyl]-4-(hexylaminocarbonylamino) benzenesulfonamide;

N-[4-[2-[[2-Hydroxy-2-(5-indolyl)ethyl]amino]ethyl] phenyl]-4-(3-octyl-2-imidazolidinon-1-yl) benzenesulfonamide;

N-[4-[2-[[2-Hydroxy-2-(5-indolyl)ethyl]amino]ethyl] phenyl]4-(3-hexyl-2-imidazolon-1-yl) benzenesulfonamide;

N-[4-[2-[[2-Hydroxy-2-(5-indolyl)ethyl]amino]ethyl] phenyl]4-[4-(3-cyclopentylpropyl)-5-tetrazolon-1-yl] benzenesulfonamide;

N-[4-[2-[[2-Hydroxy-2-(5-indolyl)ethyl]amino]ethyl] phenyl]-4-[5-(3,4-difluorobenzyl)-[1,2,4]-oxadiazol-3-yl]benzenesulfonamide;

N-[4-[2-[[2-Hydroxy-2-(5-indolyl)ethyl]amino]ethyl] phenyl]-1-[6-(3-cyclopentylpropyl)pyrid-2-yl]-5-indolinesulfonamide;

N-[4-[2-[[2-Hydroxy-2-(5-indolyl)ethyl]amino]ethyl] phenyl]-1-(6-octylpyrid-2-yl)-5-indolinesulfonamide;

N-[4-[2-[[2-(7-Aza-5-indolinyl)-2-hydroxyethyl]amino] ethyl]phenyl]-4-(3-octyl-2-imidazolidinon-1-yl) benzenesulfonamide;

N-[4-[2-[[2-(7-Aza-5-indolyl)-2-hydroxyethyl]amino]ethyl] phenyl]-4-(3-octyl-2-imidazolidinon-1-yl) benzenesulfonamide;

N-[4-[2-[[2-Hydroxy-2-(7-aza-5-indolyl)ethyl]amino]ethyl] phenyl]-4-[5-(3,4-difluorophenylmethyl)-[1,2,4]-oxadiazol-3-yl]benzenesulfonamide;

N-[4-[2-[[2-Hydroxy-2-(7-aza-5-indolyl)ethyl]amino]ethyl] phenyl]-4-(hexylaminocarbonylamino) benzenesulfonamide;

N-[4-[2-[[2-Hydroxy-2-(7-aza-5-indolyl)ethyl]amino]ethyl] phenyl]-4-(3-hexyl-2-imidazolon-1-yl) benzenesulfonamide;

N-[4-[2-[[2-Hydroxy-2-(7-aza-5-indolyl)ethyl]amino]ethyl] phenyl]-1-(4-octylthiazol-2-yl)-5-indolinesulfonamide;

N-[4-[2-[[2-Hydroxy-2-(5-furo[2,3-b]pyridinyl)ethyl] amino]ethyl]phenyl]-1-(4-octylthiazol-2-yl)-5-indolinesulfonamide;

N-[4-[2-[[2-Hydroxy-2-[5-(2,3-dihydrofuro[2,3-b]pyridin) yl]ethyl]amino]ethyl]phenyl]-1-(4-octylthiazol-2-yl)-5-indolinesulfonamide.

The compounds of the instant invention all have at least one asymmetric center as noted by the asterisk in structural Formula I. Additional asymmetric centers may be present on the molecule depending upon the nature of the various substituents on the molecule, in particular, $R^2$ and $R^3$. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the hydroxy substituent is above the plane of the structure, as seen in Formula Ia, is more active and thus more preferred over the compound in which the hydroxy substituent is below the plane of the structure.

The following stereospecific structure represents the preferred stereoisomers of the instant invention:

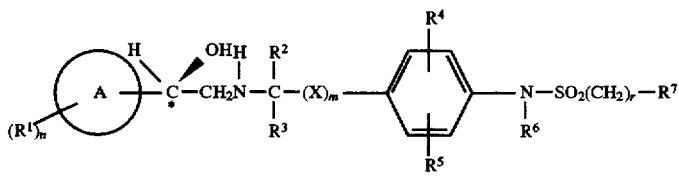

Ia where n, m, r, A, $R^1$, $R^2$, $R^3$, $R^4$, $R^5$, $R^6$, $R^7$ and X are as defined above under formula I.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atoms fluorine, chlorine, bromine and iodine.

Examples of 5 and 6-membered heterocycles and fused heterocycles of A, Z and $R^{1a}$ include pyridyl, quinolinyl, pyrimidinyl, pyrrolyl, thienyl, imidazolyl, thiazolyl, benzimidazolyl, thiadiazolyl, isoxazolyl, benzothiadiazolyl, indolyl, indolinyl, benzodioxolyl, benzodioxanyl, benzothiophenyl, benzofuranyl, benzoxazinyl, benzisoxazolyl, benzothiazolyl, tetrahydronaphthyl, dihydrobenzofuranyl, tetrahydroquinolinyl, furopyridine, tetrahydrofuropyridyl, azaindolyl, azaindolinyl and thienopyridine.

The preferred values of A and Z are phenyl, naphthyl, benzene ring fused to a 5 or 6-membered heterocyclic ring with from 1 to 4 heteroatoms selected from oxygen, sulfur and nitrogen, a 5 or 6-membered heterocyclic ring with from 1 to 2 heteroatoms selected from oxygen, sulfur and nitrogen fused to a 5 or 6-membered heterocyclic ring with from 1 to 2 heteroatoms selected from oxygen, sulfur and nitrogen, or heterocycles with from 1 to 4 heteroatoms independently selected from one of oxygen or sulfur, and/or 1 to 4 nitrogen atoms.

The more preferred values of A are quinolinyl, pyrimidinyl, pyrrolyl, thienyl, imidazolyl, and thiazolyl, isoxazolyl, indolinyl, indolyl, furopyridyl, tetrahydrofuropyridyl, 7-azaindolyl, 7-azaindolinyl.

The more preferred values of Z are phenyl, naphthyl, quinolinyl, thienyl, benzimidazolyl, thiadiazolyl, benzothiadiazolyl, indolyl, indolinyl, benzodioxolyl, benzodioxanyl, benzothiophenyl, benzofuranyl, benzoxazinyl, benzisoxazolyl, benzothiazolyl, tetrahydronaphthyl, dihydrobenzofuranyl, triazolyl, tetrazolyl, oxadiazolyl, imidazolyl, oxazolyl, thiazolyl, imidazolidinyl, pyrazolyl, isoxazolyl, pyridyl, pyrimidyl, pyrazolyl, tetrahydrobenzothiazolyl and tetrahydroquinolinyl. When Z is attached to —$NSO_2(CH_2)_r$—, it is preferably phenyl, naphthyl or a benzene ring fused to a 5 or 6-membered heterocyclic ring with from 1 to 4 heteroatoms selected from oxygen, sulfur and nitrogen. When Z is part of the definition of $R^8$, it is preferably phenyl, a 5 or 6-membered heterocyclic ring with from 1 to 4 heteroatoms selected from oxygen, sulfur and nitrogen, a benzene ring fused to a 5 or 6-membered heterocyclic ring with from 1 to 4 heteroatoms selected from oxygen, sulfur and nitrogen, or a 5 or 6-membered heterocyclic ring with from 1 to 4 heteroatoms selected from oxygen, sulfur and nitrogen fused to a $C_5$–$C_{10}$ carbocyclic ring.

The preferred heterocycles of $R^{1a}$ are thienyl, thiadiazolyl, triazolyl, tetrazolyl, oxadiazolyl, imidazolyl, oxazolyl, thiazolyl, imidazolidinyl, isoxazolyl, pyridyl, pyrimidyl, and pyrazolyl.

Certain of the above defined terms may occur more than once in the above formula and upon such occurrence each term shall be defined independently of the other; thus for example, $NR^8R^8$ may represent $NH_2$, $NHCH_3$, $N(CH_3)CH_2CH_3$, and the like.

The following abbreviations are used throughout the specification:

| Boc | tert-butyloxycarbonyl |
|---|---|
| Cbz | carbobenzyloxy |
| DIP-Cl | diisopinocampheylchloroborane |
| DMF | dimethylformamide |
| DMSO | dimethylsulfoxide |
| HPLC | high pressure liquid chromatography |
| Me | methyl |
| MPLC | medium pressure liquid chromatography |
| Ms | methanesulfonyl (mesyl) |
| NBS | N-bromosuccinimide |
| NCS | N-chlorosuccinimide |
| nHex | n-hexyl |
| TBAF | tetrabutylammonium fluoride |
| TBS (TBDMS) | t-butyldimethylsilyl |
| TFA | trifluoroacetic acid |
| THF | tetrahydrofuran |

The compounds (I) of the present invention can be prepared from epoxide intermediates such as those of formula II and amine intermediates such as those of formula III. The preparation of these intermediates is described in the following schemes.

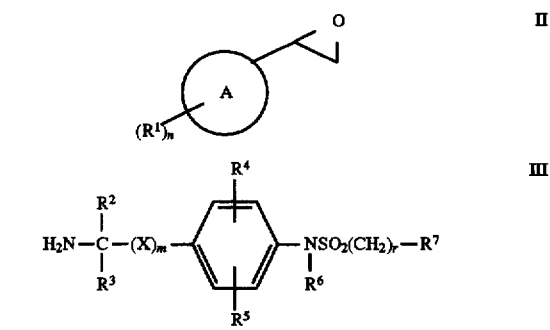

where n, m, r, A, $R^1$, $R^2$, $R^3$, $R^4$, $R^5$, $R^6$, $R^7$ and X are as defined above.

Compounds II are known in the literature or may be conveniently prepared by a variety of methods familiar to those skilled in the art. One common route is illustrated in Scheme 1. Acid chloride 1, which may be commercially available or readily prepared from the corresponding acid by treatment with, for example, thionyl chloride or oxalyl chloride, is treated with diazomethane in a solvent such as diethyl ether. The resultant diazoketone is then treated with hydrogen chloride to give chloroketone 2 (X=Cl). The haloketone 2 is then reduced with a reducing agent such as sodium borohydride. The resultant alcohol 3 is treated with base such as potassium carbonate in refluxing acetone to provide the desired epoxide II. The enantiomerically enriched (R) and (S) epoxides II are readily available by asymmetric reduction of haloketones 2 using chiral reducing agents such as (−) or (+)-DIP-Cl, (R) or (S)-Alpine borane or (R) or (S)-tetrahydro-1-methyl-3,3-diphenyl-1H,3H-pyrrolo[1,2-c][1,3,2]oxazaborole-borane ((R) or (S)-OAB.BH$_3$).

SCHEME 1

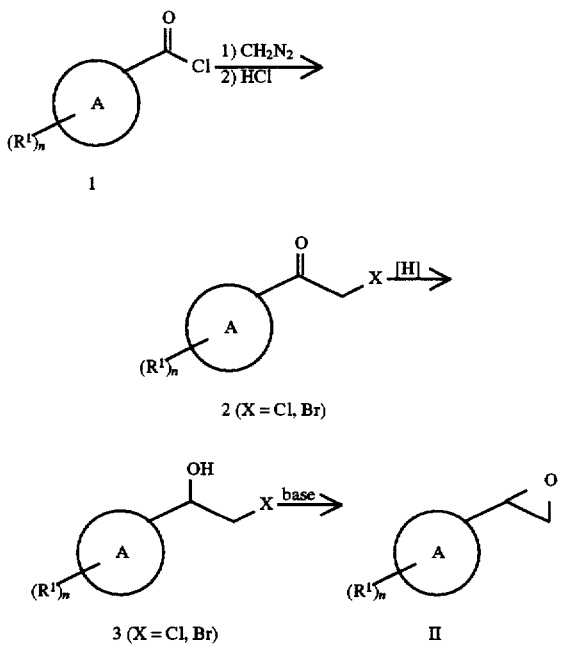

An alternate route to the desired haloketones 2 is illustrated in Scheme 2. Methylketone 4 may be converted to the corresponding haloketone using a variety of reagents known to those in the art and summarized in Larock *Comprehensive Organic Transformations*; VCH: New York, 1989, 369–372. Conveniently, methylketone 4 is treated with chlorine or N-chlorosuccinimide in acetic acid with an additional acid source such as hydrogen chloride or aluminum chloride. For the synthesis of 2 (X=Br), bromine, dibromobarbituric acid or NBS with hydrogen bromide or aluminum bromide may be used. In some cases, the chloro or bromoketones 2 may be commercially available.

SCHEME 2

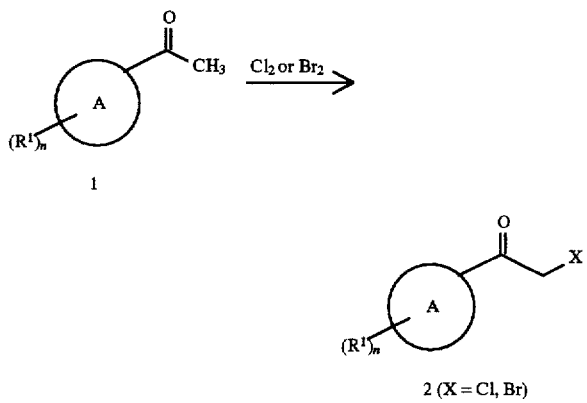

Many of the methylketones 4 are commercially available or readily prepared by methods described in the literature and known to those skilled in the art. R$^1$ substituents on the acid chlorides 1 or methylketones 4 may need to be protected during the subsequent procedures. A description of such protecting groups may be found in: *Protective Groups in Organic Synthesis*, 2nd Ed., T. W. Greene and P. G. M. Wuts, John Wiley and Sons, New York, 1991.

Compounds III can be conveniently prepared by a variety of methods familiar to those skilled in the art. A convenient route for their preparation when R$^6$ is hydrogen is illustrated in Scheme 3. Compound 5 is selectively protected as a suitable carbamate derivative 6 with, for example, di-tert-butyl dicarbonate or carbobenzyloxy chloride. This compound is then treated with a sulfonyl halide, preferably the sulfonyl chloride 7, and a base such as pyridine in an anhydrous solvent such as dichloromethane or chloroform for 0.5 to 24 hours at temperatures of −20° to 50° C., preferably 0° C., to provide the sulfonamide 8. The protecting group is then removed with, for example, trifluoroacetic acid in the case of Boc or catalytic hydrogenation in the case of Cbz, to give the desired amine 9.

SCHEME 3

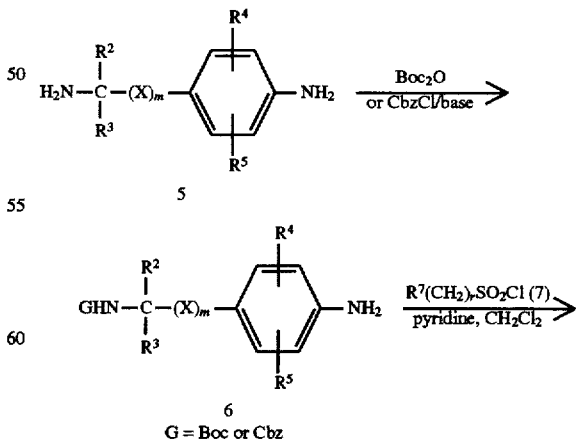

-continued
SCHEME 3

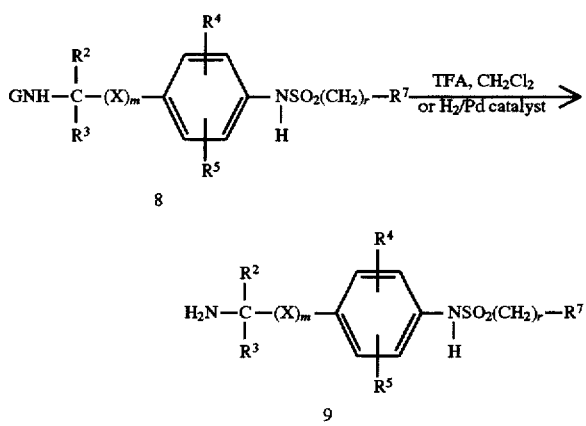

Compounds III where $R^6$ is not hydrogen may be conveniently prepared as illustrated in Scheme 4. Sulfonamide 8, prepared as described above, is alkylated with an appropriate alkylating agent 10 in the presence of base to provide sulfonamide 11. Removal of the protecting group as above gives the desired compound 9a.

SCHEME 4

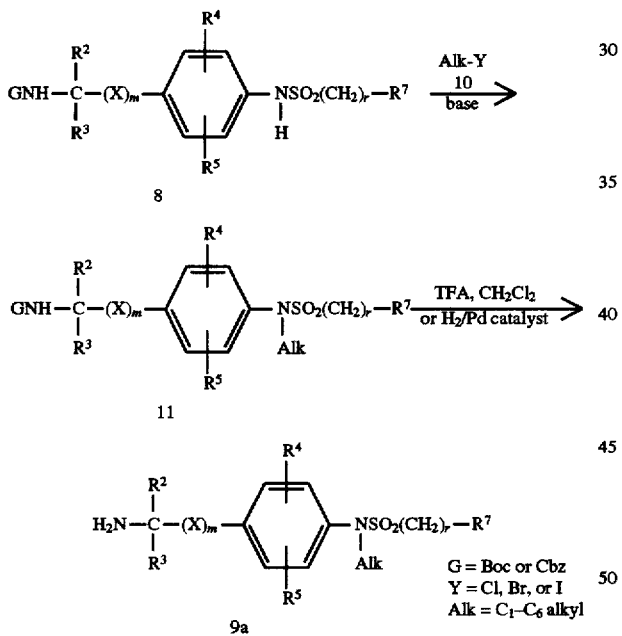

The sulfonyl chlorides 7, many of which are commercially available, can also be readily prepared by a number of methods familiar to those skilled in the art. One suitable method involves the addition of an organolithium reagent or a Grignard reagent to sulfuryl chloride following the procedure of S. N. Bhattacharya, et. al., J. Chem. Soc. (C), 1265–1267 (1969). Another convenient method involves the treatment of a thiol with sulfuryl chloride and a metal nitrate according to the procedure of Y. J. Park, et. al., Chemistry Letters, 1483–1486 (1992). Sulfonic acids are also conveniently converted to the corresponding sulfonyl chloride by treatment with $PCl_5$, $PCl_3$ or $SOCl_2$ (J. March, Advanced Organic Chemistry, 4th Ed., John Wiley and Sons, New York: 1992, p1297 and references cited therein). Aromatic and heteroaromatic compounds may be chlorosulfonylated directly by treatment with Vilsmeier's reagent or chorosulfonic acid (Organic Synthesis, I, 8).

The diamines 5 are commercially available or readily prepared by methods described in the literature or known to those skilled in the art. Compound 5 where $R^2$ or $R^3$ is methyl can be prepared from the corresponding amino acid following the method of J. D. Bloom, et. al., J. Med. Chem., 35, 3081–3084 (1992). As illustrated in Scheme 5 for $R^3$=methyl, the appropriate (R) amino acid 12 is esterified, conveniently by treatment with methanolic hydrochloric acid, and then treated with di-tert-butyl dicarbonate to give compound 13. The ester group is reduced with a hydride source such as lithium borohydride and the resultant alcohol is converted to a leaving group such as a mesylate. Removal of the Boc protecting groups gives diamine 14. This compound is subjected to catalytic hydrogenation in the presence of base such as sodium acetate to give the desired α-methyl amine 15. The other enantiomer is available through an analogous sequence starting with the corresponding (S) amino acid.

SCHEME 5

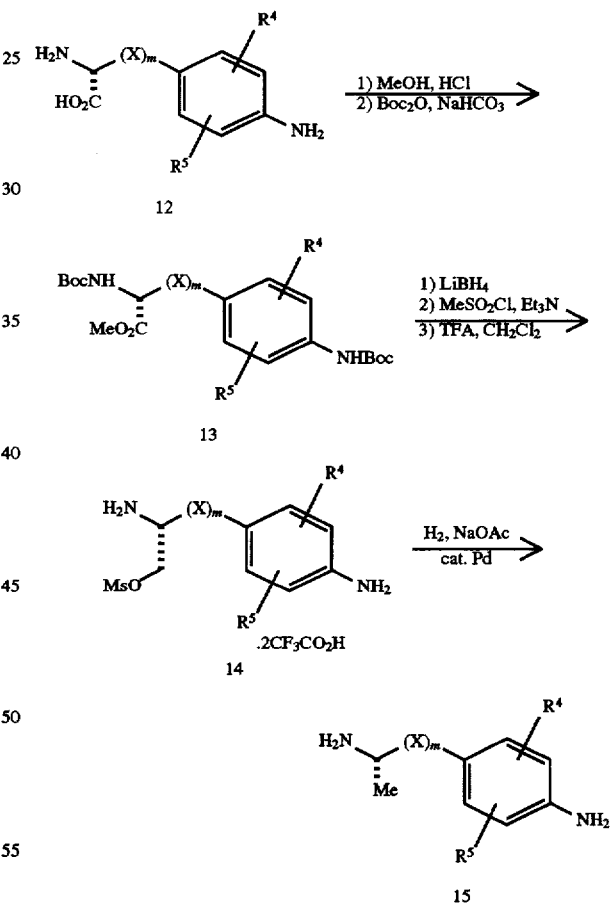

Diamines 5 or sulfonamide amines 9 where X is —$CH_2O$— and m is 1 are also readily prepared by methods described in the literature or known to those skilled in the art. For example, as shown in Scheme 6, the sodium salt of 4-nitrophenol 16 is alkylated with 1-bromo-2-chloroethane, conveninetly in refluxing 2-butanone with a base such as potassium carbonate to give chloro derivative 17. The chloride is converted to the corresponding amine by treatment with lithium azide followed by reduction with, for example, triphenylphosphine in aqueous tetrahydrofuran. Protection of the resultant amine, conveniently as its t-butyl carbamate by treatment with di-tert-butyldicarbonate, gives derivative 18. The nitro group is then reduced, for example, by catalytic hydrogenation to provide amine 19. Acylation of intermediate 19 with sulfonyl chloride 7, followed by deprotection with acid such as trifluoroacetic acid gives the desired intermediate 20.

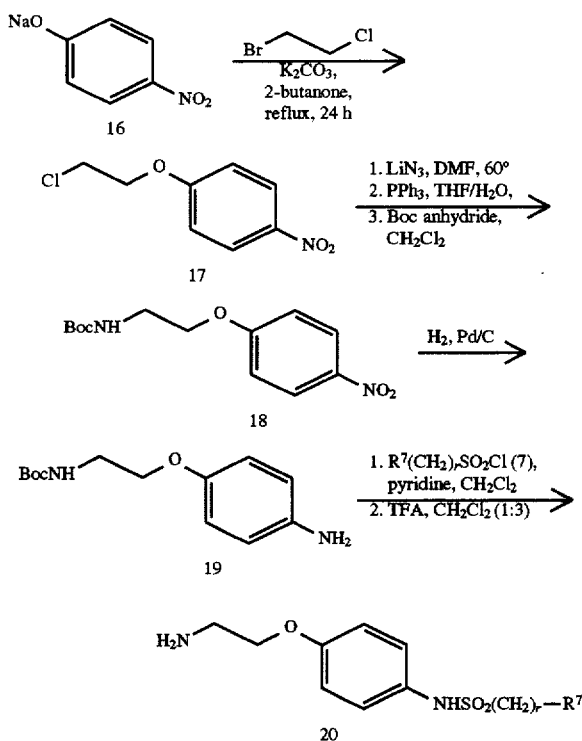

Alternatively, diamine 5 where X is —CH$_2$O— and m is 1 is available from intermediate 19 by treatment with trifluoroacetic acid. This diamine may then be modified as illustrated in Scheme 3.

Diamines 5 and sulfonamide amines 9 where X is —CH$_2$CH$_2$— and m is 1 are also readily prepared by methods described in the literature or known to those skilled in the art. For example, as shown in Scheme 7, bromo derivative 21 is treated with sodium cyanide to provide nitrile 22. The nitro group is selectively reduced by treatment with hydrogen and catalytic palladium to provide amine 23. Amine 23 is acylated with sulfonyl chloride 7 to give the corresponding sulfonamide 24. Reduction of compound 24 with cobalt chloride and sodium borohydride provides the desired amine 25.

SCHEME 7

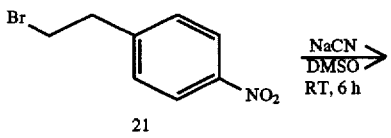

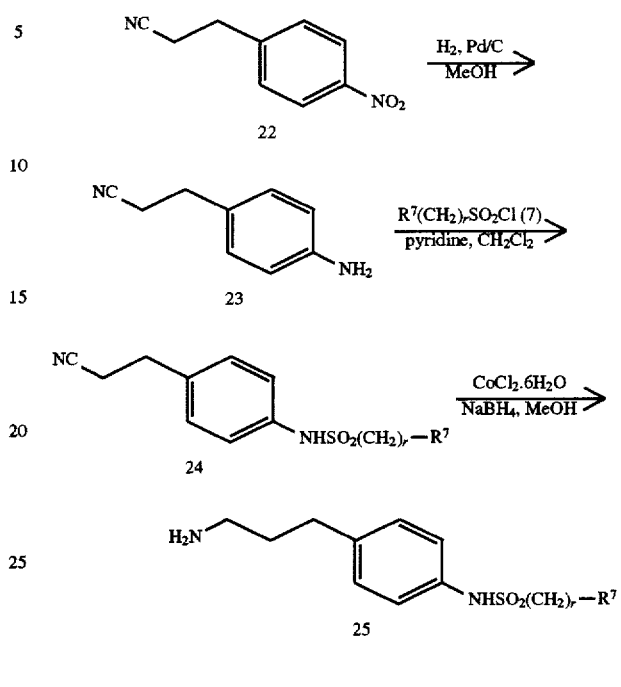

Alternatively, diamine 5 where X is —CH$_2$CH$_2$— and m is 1 is available from intermediate 23 by reduction of the nitrile group with, for example, cobalt chloride and sodium borohydride. This diamine may then be modified as illustrated in Scheme 3.

Intermediates II and III are coupled by heating them neat or as a solution in a polar solvent such as methanol, acetonitrile, tetrahydrofuran, dimethylsulfoxide or N-methyl pyrrolidinone for 1 to 24 hours at temperatures of 30° to 150° C. to provide compounds I as shown in Scheme 8. The reaction is conveniently conducted in refluxing methanol. Alternatively, a salt of amine III, such as the trifluoroacetate or hydrochloride salt, may be used. In these cases, a base such as sodium bicarbonate or diethylisopropylamine is added to the reaction mixture. The product is purified from unwanted side products by recrystallization, trituration, preparative thin layer chromatography, flash chromatography on silica gel as described by W. C. Still, et. al., J. Org. Chem. 43, 2923 (1978), medium pressure liquid chromatography, or HPLC. Compounds which are purified by HPLC may be isolated as the corresponding salt. Purification of intermediates is achieved in the same manner.

SCHEME 8

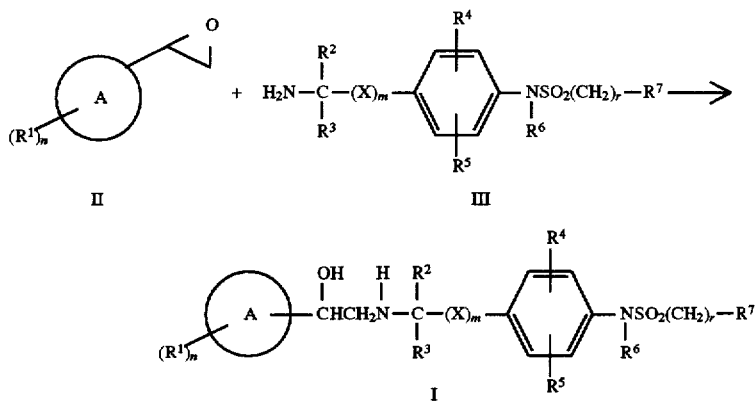

In some cases, the coupling product I from the reaction described in Scheme 8 may be further modified, for example, by the removal of protecting groups or the manipulation of substituents on, in particular, $R^1$ and $R^7$. These manipulations may include, but are not limited to, reduction, oxidation, alkylation, acylation, and hydrolysis reactions which are commonly known to those skilled in the art.

An alternate method for the synthesis of compound I is illustrated in Scheme 9. Epoxide II is coupled to amine 5 as described above for coupling intermediates II and III (Scheme 8) to give aniline derivative 27. The secondary amine is selectively protected, for example, as a carbamate by treatment with di-tert-butyldicarbonate to provide carbamate 29. Alternatively, nitro amine 26 is used in the coupling reaction to provide 28. Following protection as described above, the nitro group is reduced, for example, by catalytic hydrogenation with palladium catalyst or raney nickel, to provide intermediate 29. In some cases, other group may be reduced concomitantly. For example, if $R^1$ is halogen in intermediate 28, it may be converted to hydrogen in intermediate 29. Treatment with a sulfonyl chloride in the presence of a base such as pyridine followed by removal of the protecting group with, in the case of a tert-butylcarbamate, acid such as trifluoroacetic acid or methanolic hydrogen chloride, provides the sulfonamide I.

SCHEME 9

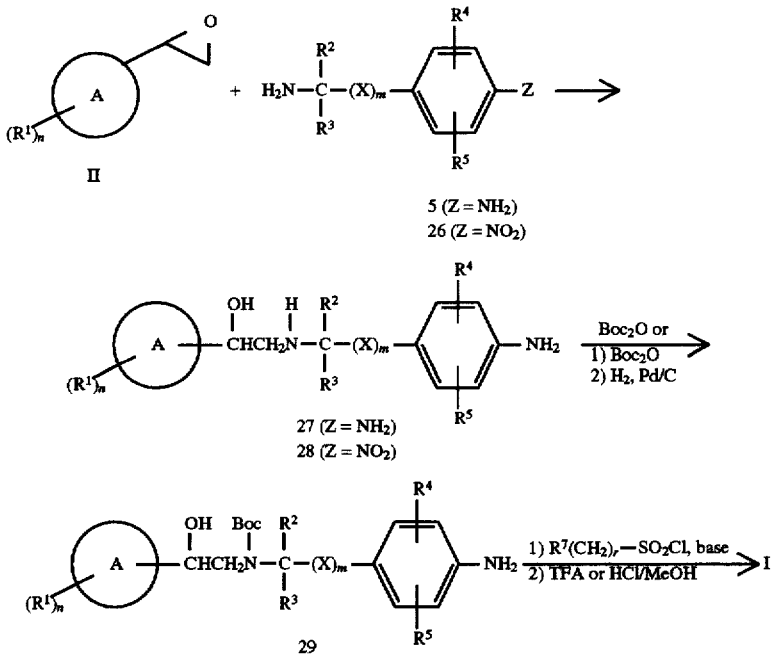

In some cases, compound I from the reaction sequence illustrated in Scheme 9 may be further modified, for example, by the removal of protecting groups or the manipulation of substituents on, in particular, $R^1$ and $R^7$, as described above. In addition, manipulation of substituents on any of the intermediates in the reaction sequence illustrated in Scheme 9 may occur. One such example is illustrated in Scheme 10. Compound 30, which is prepared as outlined in Scheme 9 from the corresponding epoxide, is subjected to reduction using tin(II) chloride to provide compound 31. Other examples of substituents on compound I which may be reduced to the corresponding amine by methods commonly known to those skilled in the art include nitro groups, nitriles, and azides.

may include, but are not limited to, reduction, oxidation, alkylation, acylation, and hydrolysis reactions which are commonly known to those skilled in the art.

An alternate synthesis of key intermediate 29 is shown is Scheme 12. The alcohol of intermediate 3 is protected, for

SCHEME 10

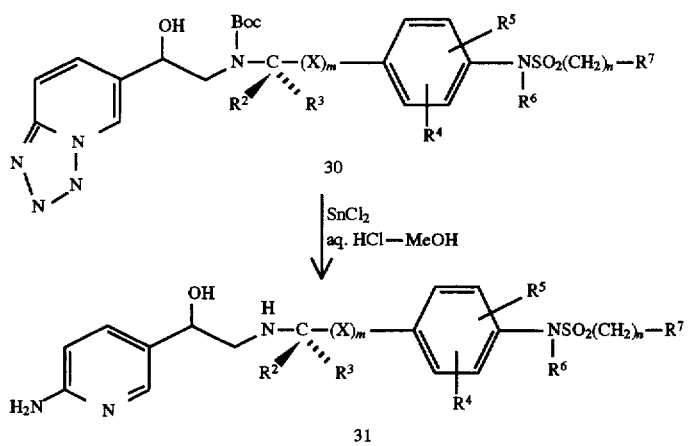

The compounds (I) of the present invention can also be prepared from amine intermediates such as those of formula III and haloketone intermediates such as those of formula 2, as shown in Scheme 11. Amine III is alkylated with haloketone derivative 2, conveniently by treatment of a mixture of III and 2 with base such as potassium carbonate or triethylamine in a polar solvent such as acetonitrile, acetone or dimethylformamide. The resultant aminoketone 32 is reduced with, for example, sodium borohydride in methanol to give the desired aminoalcohol I.

example, as its t-butyldimethylsilyl ether to give TBS derivative 33. This compound is then treated with amine 5 and a base such as diisopropylethylamine in a solvent, typically polar aprotic such as acetonitrile, at temperatures of 25° to 150° C. for 1 to 72 hours. Typically, an iodide source such as sodium iodide is added to facilitate the reaction. The protecting group is then removed, in the case of silyl ether, by treatment of the resultant amine 34 with a fluoride source such as tetrabutylammonium fluoride. Pro-

SCHEME 11

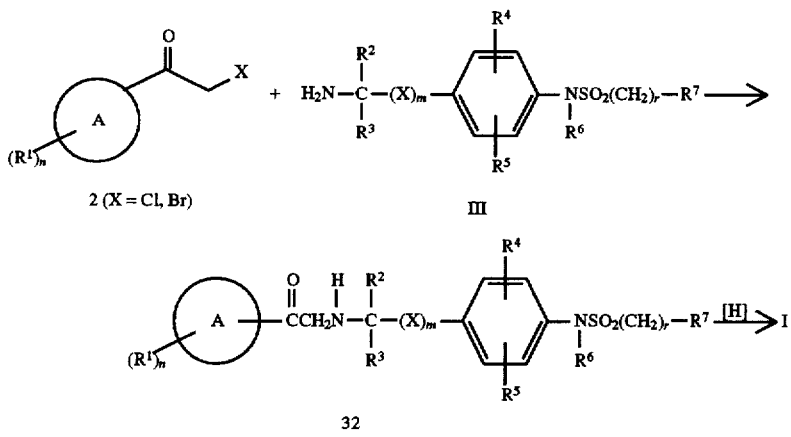

In some cases, the product I from the reaction described in Scheme 11 may be further modified, for example, by the removal of protecting groups or the manipulation of substituents on, in particular, $R^1$ and $R^7$. These manipulations tection of the secondary amine as before gives key intermediate 29. Alternatively, the silyl protecting group may be carried through the synthesis and removed in the final deprotection step.

SCHEME 12

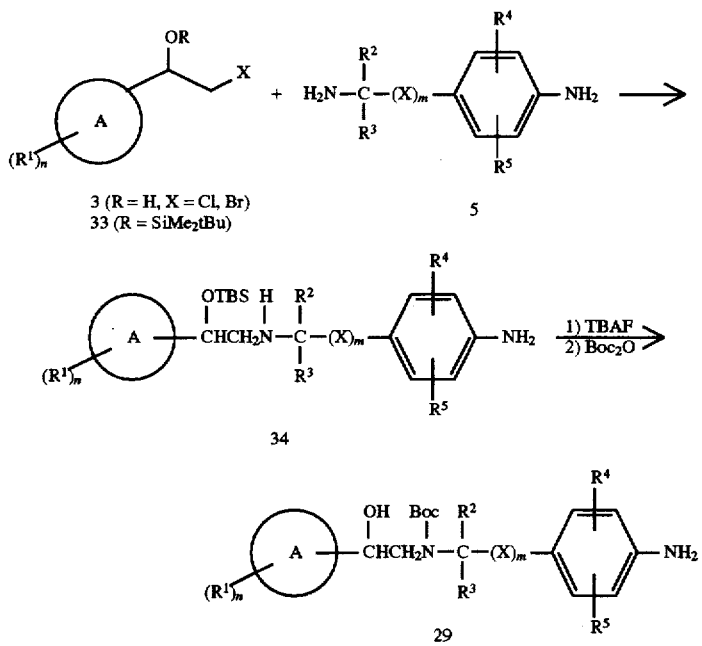

In some cases, compound I may be synthesized directly from intermediate 27 without protection of the secondary amine. For example, when $R^2$ and $R^3$ are both methyl, aniline derivative 27 is treated with sulfonyl chloride 7 and a base such as pyridine in a solvent such as dichloromethane at a temperature of −30° to 50° C., typically 0° C., to provide compound I.

In some cases, the product I from the reaction described in Scheme 13 may be further modified, for example, by the removal of protecting groups or the manipulation of substituents on, in particular, $R^1$ and $R^7$, as described above.

shown in Scheme 14. Acid 36 is available from the corresponding ester 35, typically a methyl or ethyl ester, by treatment with sulfonyl chloride 7 and a base such as pyridine, followed by hydrolysis of the ester with aqueous acid or base. Acid 36 is coupled to amine 37, which is known in the literature or readily prepared by methods known to those skilled in the art, using a coupling agent such as benzotriazolyl-N-oxy-tris(dimethylamino)phosphonium hexafluorophosphate or 1-(3-dimethylaminopropyl)-3-ethylcarbodiimide methiodide to provide the amide 38. This is treated with a reducing agent, typically borane, to provide the desired compound I.

SCHEME 13

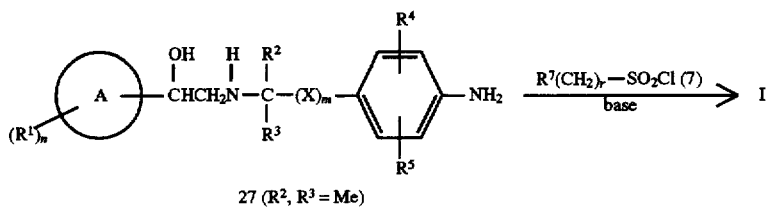

The compounds (I) of the present invention where $R^2$ and $R^3$ are hydrogen can also be prepared from acid intermediates of formula 36 and aminoalcohols of formula 37, as

SCHEME 14

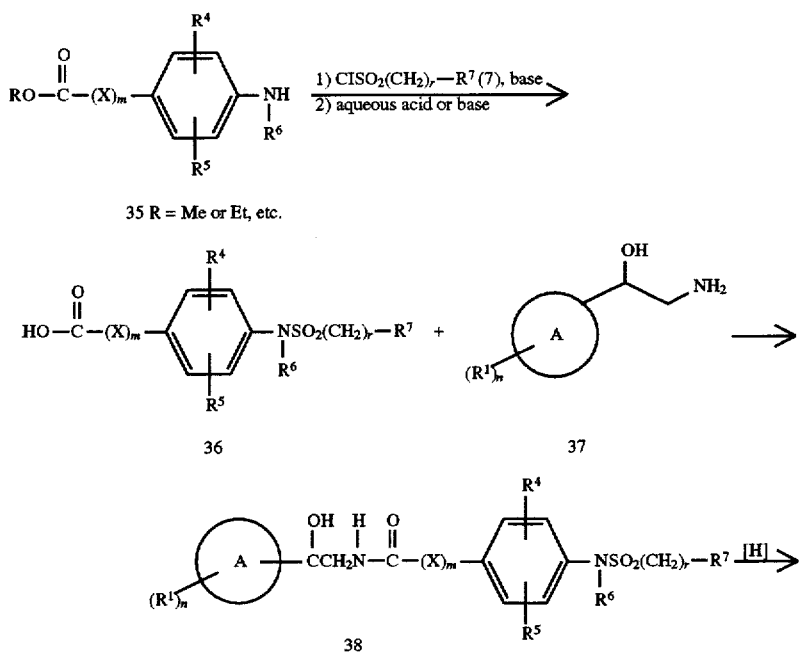

35 R = Me or Et, etc.

Compounds of the general Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I may be obtained by stereospecific synthesis using optically pure starting materials of known configuration.

The instant compounds can be isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy or tetrazole, can be isolated in the form of their inorganic salt in which the counterion can be selected from sodium, potassium, lithium, calcium, magnesium and the like, as well as from organic bases.

As previously indicated, the compounds of the present invention have valuable pharmacological properties.

The present invention also provides a compound of the general Formula I or a pharmaceutically acceptable salt thereof for use as an active therapeutic substance.

In one aspect, the present invention provides a compound of the general Formula I or a pharmaceutically acceptable ester thereof; or a pharmaceutically acceptable salt thereof for use in the treatment of obesity in human or non-human animals.

The present invention further provides a compound of the general Formula I, or a pharmaceutically acceptable ester thereof; or pharmaceutically acceptable salt thereof, for use in the treatment of hyperglycemia (diabetes) in human or non-human animals.

The disease diabetes mellitus is characterized by metabolic defects in production and utilization of glucose which result in the failure to maintain appropriate blood sugar levels. The result of these defects is elevated blood glucose or hyperglycemia. Research on the treatment of diabetes has centered on attempts to normalize fasting and postprandial blood glucose levels. Treatments have included parenteral administration of exogenous insulin, oral administration of drugs and dietary therapies.

Two major forms of diabetes mellitus are now recognized. Type I diabetes, or insulin-dependent diabetes, is the result of an absolute deficiency of insulin, the hormone which regulates glucose utilization. Type II diabetes, or insulin-independent diabetes, often occurs in the face of normal, or even elevated levels of insulin and appears to be the result of the inability of tissues to respond appropriately to insulin. Most of the Type II diabetics are also obese.

In addition the compounds of the present invention lower triglyceride levels and cholesterol levels and raise high density lipoprotein levels and are therefore of use in combatting medical conditions wherein such lowering (and raising) is thought to be beneficial. Thus they may be used in the treatment of hyper-triglyceridaemia, hypercholesterolaemia and conditions of low HDL (high density lipoprotein) levels in addition to the treatment of atherosclerotic disease such as of coronary, cerebrovascular and peripheral arteries, cardiovascular disease and related conditions.

Accordingly, in another aspect the present invention provides a method of lowering triglyceride and/or cholesterol levels and/or increasing high density lipoprotein levels which comprises administering, to a human or a non-human animal in need thereof, a therapeutically effective amount of a compound of the formula (I) or pharmaceutically acceptable salt thereof. In a further aspect the present invention provides a method of treating atherosclerosis which comprises administering, to an animal in need thereof; a therapeutically effective amount of a compound of the formula (I) or pharmaceutically acceptable salt thereof. The compositions are formulated and administered in the same general manner as detailed below for treating diabetes and obesity. They may also contain other active ingredients known for use in the treatment of atherosclerosis and related conditions, for example fibrates such as clofibrate, bezafibrate and gemfibrozil; inhibitors of cholesterol biosynthesis such as HMG-CoA reductase inhibitors for example lovastatin, simvastatin and pravastatin; inhibitors of cholesterol absorption for example beta-sitosterol and (acyl CoA:cholesterol acyltransferase) inhibitors for example melinamide; anion exchange resins for example cholestyramine, colestipol or a dialkylaminoalkyl derivatives of a cross-linKed dextran; nicotinyl alcohol, nicotinic acid or a salt thereof; vitamin E; and thyromimetics.

The compounds of the instant invention also have the effect of reducing intestinal motility and thus find utility as aiding in the treatment of various gastrointestinal disorders such as irritable bowel syndrome. It has been proposed that the motility of non-sphincteric smooth muscle contraction is mediated by activity at $\beta_3$ adrenoreceptors. The availability of a $\beta_3$ specific agonist, with little activity at $\beta_1$ and $\beta_2$ receptors will assist in the pharmacologic control of intestinal motility without concurrent cardiovascular effects. The instant compounds are administered generally as described below with dosages similar to those used for the treatment of diabetes and obesity.

It has also been found unexpectedly that the compounds which act as agonists at $\beta_3$ adrenoreceptors may be useful in the treatment of gastrointestinal disorders, especially peptic ulcerations, esophagitis, gastritis and duodenitis, (including that induced by *H. pylori*), intestinal ulcerations (including inflammatory bowel disease, ulcerative colitis, Crohn's disease and proctitis) and gastrointestinal ulcerations.

In addition, $\beta_3$ receptors have been indicated to have an effect on the inhibition of the release of neuropeptides in certain sensory fibers in the lung. As sensory nerves may play an important role in the neurogenic inflammation of airways, including cough, the instant specific $\beta_3$ agonists may be useful in the treatment of neurogenetic inflammation, such as asthma, with minimal effects on the cardio-pulmonary system.

$\beta_3$ adrenoreceptors are also able to produce selective antidepressant effects by stimulating the $\beta_3$ receptors in the brain and thus an additional contemplated utility of the compounds of this invention are as antidepressant agents.

The active compounds of the present invention may be orally administered as a pharmaceutical composition, for example, with an inert diluent, or with an assimilable edible carrier, or they may be enclosed in hard or soft shell capsules, or they may be compressed into tablets, or they may be incorporated directly with the food of the diet. For oral therapeutic administration, which includes sublingual administration, these active compounds may be incorporated with excipients and used in the form of tablets, pills, capsules, ampules, sachets, elixirs, suspensions, syrups, and the like. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The effective dosage of active ingredient employed may vary depending on the particular compound employed, the mode of administration, the condition being treated and the severity of the condition being treated.

When treating diabetes mellitus and/or hyperglycemia generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

When treating obesity, in conjunction with diabetes and/or hyperglycemia, or alone, generally satisfactory results are obtained when the compounds of the present invention are administered at a daily dosage of from 0.01 milligram to about 100 milligrams per kilogram of animal body weight, preferably given in a single dose or in divided doses two to six times a day, or in sustained release form. In the case of a 70 kg adult human, the total daily dose will generally be from about 0.7 milligrams to about 3500 milligrams. This dosage regimen may be adjusted to provide the optimal therapeutic response.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The following examples are provided so that the invention might be more fully understood. They should not be construed as limiting the invention in any way.

EXAMPLE 1

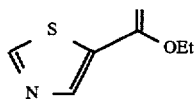

5-(1-Ethoxyvinyl)thiazole

A mixture of 3.28 g (20.0 mmol) of 5-bromothiazole (for synthesis see H. C. Beyerman, P. H. Berben, J. S. Bontekoe, Rec. Trav. Chim. 1954, 73, 325), 7.43 mL (22.0 mmol) of (1-ethoxyvinyl)tributyltin, and 284 mg (0.404 mmol) of $PdCl_2(PPh_3)_2$ in 40 mL of DMF was heated at 70° C. for 30 h. The reaction mixture was cooled to 0° C. and 40 mL of a solution of potassium fluoride in water and 40 mL of diethyl ether were added. After stirring for 40 min the precipitate was filtered off and the aqueous and organic phases separated. The aqueous phase was re-extracted with 4×40 mL of diethyl ether. The combined ether phases were washed with 2×75 mL of water, 1×100 mL of brine, dried ($MgSO_4$) and the solvent removed in vacuo. Flash chromatography (silica gel, 20% ethyl acetate-hexanes) afforded 2.58 g (83%) of the title compound as a yellow oil: $^1H$ NMR (400 MHz, $CDCl_3$) δ8.65 (s, 1H), 7.80 (s, 1H), 4.61 (d, 1H, J=3 Hz), 4.24 (d, 1H, J=3 Hz), 3.91 (q, 2H, J=7 Hz), 13.9 (t, 3H, J=7 Hz).

EXAMPLE 2

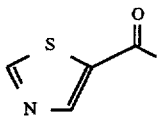

Six drops of 2N aqueous HCl were added to a solution of 310 mg (2.0 mmol) of the product from Example 1 in 20 mL of acetone. After stirring for 20 min, ~50% of the acetone was removed in vacuo, and 25 mL of $CHCl_3$, 10 ml of saturated $NaH_2PO_4$ and 30 mL of water were added. The organic phase was separated and the aqueous phase re-extracted with 15 mL of $CHCl_3$. The combined organic phase was washed with brine, dried ($MgSO_4$) and the solvent removed in vacuo to afford 235 mg (93%) of the title compound as a yellow solid: $^1H$ NMR (400 MHz, $CDCl_3$) δ8.98 (s, 1H), 8.41 (s, 1H), 2.61 (s, 3H).

EXAMPLE 3

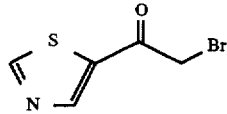

5-(2-Bromoacetyl)thiazole

A solution of 699 mg (2.44 mmol) of dibromobarbituric acid in 10 mL of THF was added to a solution of 444 mg (3.49 mmol) of the product from Example 2 in 10 mL of THF. The solution was heated at reflux for 19 h. After cooling to room temperature, 50 mL of diethyl ether was added. The mixture was washed with 25 mL of saturated aqueous sodium bicarbonate solution. The sodium bicarbonate wash was back-extracted with 15 mL of diethyl ether. The combined organic phase was washed with brine, dried ($MgSO_4$) and the solvent removed in vacuo. Flash chromatography (silica gel, 15% diethyl ether-dichloromethane) afforded 300 mg (42%) of the title compound as white crystals: $^1H$ NMR (400 MHz, $CDCl_3$) δ9.04 (s, 1H), 8.54 (s, 1H), 4.34 (s, 2H).

EXAMPLE 4

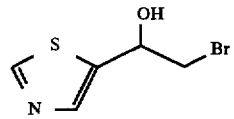

α-Bromomethyl-5-thiazolemethanol

Sodium borohydride (38 mg, 1.0 mmol) was added in one portion to a solution of 207 mg (1.0 mmol) of the product from Example 3 in 2 mL of methanol at 0° C. After stirring for 0.75 h, water was added and the mixture extracted three times with diethyl ether. The combined organic phase was washed with brine, dried($MgSO_4$) and the solvent removed in vacuo. Flash chromatography (silica gel, 30–40% ethyl acetate-hexanes) afforded 130 mg (62%) of the title compound as a colorless oil: $^1H$ NMR (400 MHz, $CDCl_3$) δ8.78 (s, 1H), 7.83 (s, 1H), 5.28–5.24 (m, 1H), 3.70 (dd, 1H, J=10.6, 3.9 Hz), 3.61 (dd, 1H, J=10.6, 7.9 Hz), 2.95 (d, 1H, J=4.3 Hz).

EXAMPLE 5

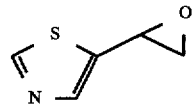

Thiazol-5-yloxirane

Potassium carbonate (422 mg, 3.05 mmol) was added in one portion to a solution of 127 mg (0.610 mmol) of the product from Example 4 in 5 mL of acetone. After stirring for 14 h the solids were filtered off and the filtrate evaporated in vacuo. Flash chromatography (silica gel, 5–10% diethyl ether-dichloromethane) afforded 71.2 mg (92%) of the title compound as a colorless oil: $^1H$ NMR (500 MHz, $CDCl_3$) δ8.76 (s, 1H), 7.94 (s, 1H), 4.19–4.17 (m, 1H), 3.26 (dd, 1H, J=5.0, 2.5 Hz), 2.99 (dd, 1H, J=5.0, 4.1 Hz).

EXAMPLE 6

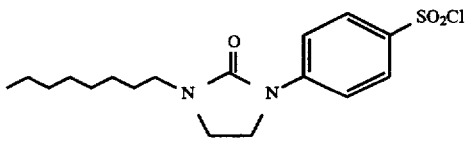

4-(3-octyl-2-imidazolidinon-1-yl)benzenesulfonyl chloride

To a 0° C. suspension of 5.00 g (30.8 mmol) 1-phenylimidazolidin-2-one in 50 mL of dimethylformamide was added 1.48 g (37.0 mmol, 1.2 equiv) of sodium hydride (60% oil dispersion). After 45 minutes, 6.7 mL (8.88 g, 37.0 mmol, 1.2 equiv) of octyl iodide was added. The mixture was allowed to stir overnight with gradual warming to room temperature. TLC analysis indicated the presence of starting material. An additional 830 mg portion of sodium hydride was added. After 5 hours, TLC analysis again indicated the presence of starting material, so 0.5 g more sodium hydride and 6 mL of octyl iodide were added. After 2 hours, the reaction was complete as judged by TLC analysis. The mixture was concentrated in vacuo, and partitioned between 200 mL of ethyl acetate and 50 mL of water. The organic phase was washed sequentially with three 50-mL portions of water and one portion of brine, dried over magnesium sulfate, and concentrated in vacuo. Purification by flash chromatography (silica gel, 10–25% ethyl acetate/hexane) provided 3.97 g (47%) of 3-octyl-1-phenylimidazolidin-2-one. A 3.93 g portion of this material was added over 45 min to 6 mL of chlorosulfonic acid in a salt/ice bath. Stirring was continued at −5° C. until gas evolution ceased (~3 hours). The reaction mixture was poured into 50 mL of ice and extracted with 3 150-mL portions of ethyl acetate. The combined organic phases were dried over magnesium sulfate and concentrated in vacuo. Purification by flash chromatography (25% ethyl acetate/hexane) provided 2.49 g of the title compound: $^1$H NMR (500 MHz, CDCl$_3$) δ7.94 (d, 2H), 7.76 (d, 2H), 3.87 (dd, 2H), 3.55 (dd, 2H), 3.31 (t, 2H), 1.56 (m, 2H), 1.36–1.21 (m, 10H), 0.85 (m, 3H).

EXAMPLE 7

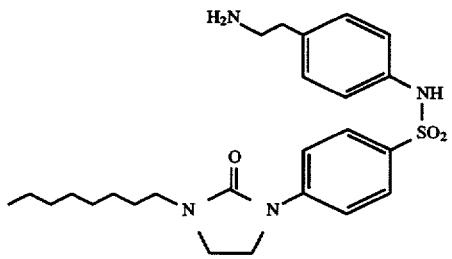

N-[4-(2-aminoethyl)phenyl]-4-(3-octyl-2-imidazolidinon-1-yl)benzensulfonamide

A solution of 118 mg (0.499 mmol) of 2-(4-aminophenyl)ethylcarbamic acid 1,1-dimethylethyl ester (for synthesis see M. H. Fisher, E. R. Parmee, M. R. Mathvink, A. E. Weber, European Patent Application 0 611 003 A1) in 5 mL of dichloromethane was treated with 195.7 mg (0.525 mmol) of 4-(3-octyl-2-imidazolidinon-1-yl)benzenesulfonyl chloride from Example 6 and 40 µL (0.495 mmol) of pyridine. After stirring for 16 h, 1.5 mL of trifluoroacetic acid was added and the reaction mixture stirred for 0.75 h. The volatile components were removed in vacuo. Flash chromatography (silica gel, 5–10% (10% ammonia-methanol)-methylene chloride) afforded 204 mg (86%) of the title compound as a white powder: $^1$H NMR (400 MHz, CDCl$_3$) δ7.65 (d, 2H, J=9.2 Hz), 7.58 (d, 2H, J=9.2 Hz), 7.03 (d, 2H, J=8.6 Hz), 6.96 (d, 2H, J=8.5 Hz), 3.80–3.76 (m, 2H), 3.50–3.46 (m, 2H), 3.26 (t, 2H, J=7.4 Hz), 2.88 (t, 2H, 6.8 Hz), 2.65 (t, 2H, J=6.9 Hz) 1.65–1.60 (m, 2H), 1.29–1.23 (m, 10H), 0.85 (m, 3H).

EXAMPLE 8

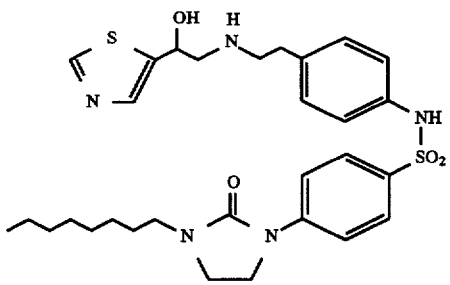

N-[4-[2-[[2-Hydroxy-2-(thiazol-5-yl)ethyl]amino]ethyl]phenyl]-4-(3-octyl-2-imidazolidinon-1-yl)benzenesulfonamide A solution of 20 mg (0.157 mmol) of the compound from Example 5 in 0.5 mL of methanol was added to a suspension of 89.2 mg (0.190 mmol) of the compound from Example 7 in 1 mL of methanol. The mixture was heated at reflux for 15 h. Flash chromatography (silica gel, 5–10% methanol-dichloromethane) afforded 33.2 mg (35%) of the title compound as a glass: $^1$H NMR (500 MHz, CD$_3$OD) δ8.89 (s, 1H), 7.75 (s, 1H), 7.63 (m, 4H), 7.06 (d, 2H, J=8.5 Hz), 7.00 (d, 2H, J=8.5 Hz), 5.07–5.05 (m, 1H), 3.85–3.81 (m, 2H), 3.53–3.50 (m, 2H), 3.25 (t, 2H, J=7.3 Hz), 2.87–2.71 (m, 6H), 1.59–1.55 (m, 2H), 1.33–1.29 (m, 10H), 0.88 (t, 3H, J=6.7 Hz).

Following the procedures outlined for Examples 1–8, the compounds listed in Table 1 were prepared.

TABLE 1

| | OH H | |
|---|---|---|
| (structure shown) | | |

| Example | R | Selected $^1$H NMR (CD$_3$OD) Data |
|---|---|---|
| 9 | 4-(hexylaminocarbonylamino)phenyl, trifluoroacetate salt | 9.01(s, 1H), 7.87(s, 1H), 7.60(d, 2H, J=8.8Hz), 7.43(d, 2H, J=8.8 Hz), 7.14(d, 2H, J=8.5Hz), 7.07 (d, 2H, J=8.5Hz), 5.34–5.31(m, 1H), 3.28–3.15(m, 4H), 2.95–2.91 (m, 2H), 1.52–1.49(m, 2H), 1.34–1.32(m, 8H), 0.92–0.89(m, 3H). |
| 10 | 4-iodophenyl | 8.89(s, 1H), 7.84(d, 2H, J=8.7 Hz), 7.76(s, 1H), 7.43(d, 2H, J=8.7Hz), 7.09(d, 2H, J=8.5Hz), 7.00(d, 2H, J=8.5Hz). |

EXAMPLE 11

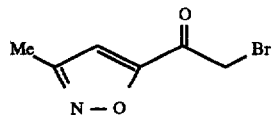

5-(2-Bromoacetyl)-3-methylisoxazole

A solution of 0.43 g (3.43 mmol) of 5-acetyl-3-methylisoxazole (for synthesis see S. Chimichi, B. Cosimelli, Synth. Comm. 1992, 22, 2909–2920) in 10 mL of THF was added to a solution of 688 mg (2.41 mmol) of dibromobarbituric acid in 10 mL of THF. The colorless solution was heated at reflux for 20 h, cooled to room temperature and partitioned between ethyl acetate and saturated aqueous sodium bicarbonate solution. The organic phase was separated and the aqueous phase re-extracted with ethyl acetate. The combined organic phase was washed with water, brine, dried(MgSO$_4$) and the solvent removed in vacuo. Flash chromatography (silica gel, 40–50% dichloromethane-hexanes) afforded 337 mg (48%) of the title compound: $^1$H NMR (400 MHz, CDCl$_3$) 6.87 (s, 1H), 4.39 (s, 2H), 2.38 (s, 3H).

EXAMPLE 12

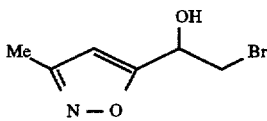

α-Bromomethyl-5-(3-methylisoxazole)methanol

Sodium borohydride (10.0 mg, 0.264 mmol) was added in one portion to a solution of 53.8 mg (0.264 mmol) of the product from Example 11 in 1 mL of methanol at 0° C. After stirring at 0° C. for 1 h saturated aqueous $NaH_2PO_4$ solution was added and the mixture extracted with diethyl ether twice. The combined organic phase was washed with brine, dried($MgSO_4$) and the solvent removed in vacuo to leave 54.4 mg (100%) of the title compound as a colorless oil: $^1H$ NMR (400 MHz, $CDCl_3$) δ6.15 (s, 1H), 5.04 (m, 1H), 3.77 (dd, 1H, J=10.7, 4.1 Hz), 3.68 (dd, 1H, J=10.7, 6.5 Hz), 2.29 (s, 3H).

EXAMPLE 13

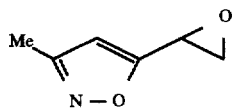

(3-Methyl-5-isoxazolyl)oxirane

To a solution of 367 mg (1.78 mmol) of the product from Example 12 in 15 mL of acetone was added 1.40 g of solid potassium carbonate. The mixture was heated at reflux for 24 h. After cooling to room temperature the mixture was filtered and the filtrate evaporated in vacuo. Flash chromatography (silica gel, 5–10% ethyl acetate-hexanes) afforded 102 mg (46%) of the title compound as a pale yellow liquid: $^1H$ NMR (400 MHz, $CDCl_3$) δ6.08 (s, 1H), 3.93 (dd, 1H, J=4.1, 2.6 Hz), 3.17 (dd, 1H, J=5.5, 4.1 Hz), 3.11 (dd, 1H, J=5.5, 2.6 Hz), 2.27 (s, 3H).

EXAMPLE 14

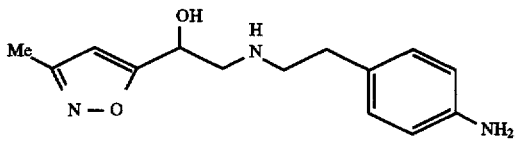

N-[2-[4-(Aminophenyl)]ethyl]-2-hydroxy-2-(3-methylisoxazol-5-yl)ethylamine

A solution of 100 mg (0.799 mmol) of the product from Example 13 in 3 mL of methanol was added dropwise to a solution of 334 μL (2.40 mmol) of triethylamine and 486 mg (2.40 mmol) of p-nitrophenethylamine hydrochloride in 8 mL of methanol. The orange solution was heated at reflux for 16 h. After cooling to room temperature the solvent was removed in vacuo. Flash chromatography (silica gel, 1–3% methanol-$CH_2Cl_2$) afforded 113 mg (49%) of the title compound as a colorless oil: $^1H$ NMR (400 MHz, $CDCl_3$) δ8.14 (d, 2H, J=8.6 Hz), 7.33 (d, 2H, J=8.6 Hz), 6.04 (s, 1H), 4.79 (m, 1H), 3.08–2.80 (m, 6H), 2.26 (s, 3H).

EXAMPLE 15

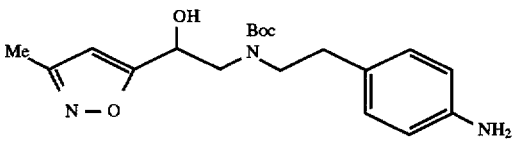

N-[2-[4-(aminophenyl)]ethyl]-2-hydroxy-2-(3-methylisoxazol-5-yl)ethylcarbamic acid 1,1-dimethylethyl ester To a solution of 111 mg (0.381 mmol) of the product from Example 4 in 8 mL of THF was added in one portion 99.8 mg (0.457 mmol) of di-tert-butyl dicarbonate. The solution was stirred for 48 h then the solvent removed in vacuo. Flash chromatography (silica gel, 30–40% ethyl acetate-hexanes) afforded 140 mg (94%) of the title compound as a colorless oil: $^1H$ NMR (400 MHz, $CDCl_3$) δ8.14 (d, 1H, J=8.3 Hz), 7.28 (d, 2H, J=8.3 Hz), 6.12 (s, 1H), 4.95 (m, 2H), 3.68–3.20 (m, 4H), 3.00–2.72 (m, 2H), 2.26 (s, 3H), 1.40 (s, 9H).

EXAMPLE 16

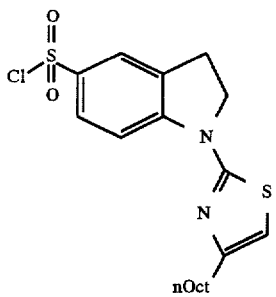

1-(4-Octylthiazol-2yl)-5-indolinesulfonyl chloride

Step A

Preparation of 5-Bromoindoline-1-thiocarboxamide

A solution of 5-bromoindoline (14.8 g, 75 mmol) in 200 mL of 1N aqueous hydrochloric acid was treated with potassium thiocyanate (34.0 g, 350 mmol) in portions. The mixture was heated at reflux for 1 h and was then cooled to room temperature. The precipitate was collected, washed with water, and recrystallized from 2-propanol to afford (in two crops) 14.1 g (73%) of 5-bromoindoline-1-thiocarboxamide as a light yellow, fluffy solid.

Step B

Preparation of 5-Bromo-1-(4-octylthiazol-2-yl)-5-indoline

A mixture of the product from Step A (3.40 g, 13.2 mmol) and 1-chloro-2-octanone (2.28 g, 12.0 mmol) in 70 mL dioxane was warmed at reflux for 18 h. After cooling to room temperature, the solvent was removed under reduced pressure, and the residual viscous oil was purified by flash chromatography (2%, then 5% EtOAc-hexane eluant) to give 2.82 g (59%) of 5-bromo-1-(4-octylthiazol-2-yl)-5-indoline as an off-white solid: $^1H$ NMR (400 MHz, $CDCl_3$, ppm) 0.86 (3H, t, J=7.0 Hz), 1.2–1.4 (10H, m), 1.70 (2H, m), 2.64 (2H, t, J=7.0 Hz), 3.23 (2H, t, J=8.6 Hz), 4.04 (2H, t, J=8.6 Hz), 6.25 (1H, s), 7.28 (2H, m), 7.89 (1H, d, J=8.5 Hz).

Step C

Preparation of 1-(4-Octylthiazol-2-yl)-5-indolinesulfonyl chloride

A solution of the product from Step B (2.17 g, 5.5 mmol) in 40 mL of dry tetrahydrofuran was cooled to –78° C. The white suspension was treated dropwise with n-butyllithium (3.8 mL of 1.6M in hexane, 6.1 mmol). After 30 min, a stream of sulfur dioxide gas was introduced over the top of the yellow aryllithium solution for 10 min. The resulting orange solution was stirred for an additional 15 min at −78° C., and was then allowed to warm to room temperature over a period of one hour. The mixture was concentrated under reduced pressure, and the residue was triturated twice with a 1:1 solution of ether:hexane. The residual lithium sulfinate salt (2.33 g) was dried in vacuo, and was subsequently suspended in 15 mL of dichloromethane. The suspension was cooled to 0° C., and N-chlorosuccinimide (0.77 g, 5.75 mmol) was added in several portions. After stirring at 0° C. for an additional 15 min, the cooling bath was removed and the mixture was allowed to warm to room temperature. After 15 min, an additional 40 mL of dichloromethane was added, and the mixture was filtered through a pad of Celite. The filtrate was concentrated under reduced pressure, and the residue was purified by flash chromatography (20% EtOAc-hexane eluant) to afford 1.60 g (70%) of a bright yellow solid: $^1$H NMR (400 MHz, CDCl$_3$, ppm) 0.86 (3H, t, J=6.8 Hz), 1.20–1.40 (10H, m), 1.68 (2H, m), 2.67 (2H, t, J=7.2 Hz), 3.35 (2H, t, J=8.8 Hz), 4.17 (2H, t, J=8.8 Hz), 6.40 (1H, s), 7.76 (1H, d, J=2.1 Hz), 7.90 (1H, dd, J=8.7 and 2.1 Hz), 8.25 (1H, d, J=8.7 Hz).

To a solution of 9.9 mg (0.274 mmol) of the compound from Example 15 and 4.4 µL (0.0544 mmol) of pyridine in 1 mL of dichloromethane was added 17.0 mg (0.0412 mmol) of 5-(1-(4-octylthiazol-2-yl))indolinesulfonyl chloride from Example 16. After stirring for 12 h, the volatile components were removed in vacuo. Flash chromatography (silica gel, 40% ethyl acetate-hexanes) afforded 16.7 mg (83%) of the Boc-protected title compound as a colorless oil.

A solution of 16.7 mg (0.0226 mmol) of Boc-protected title compound in 1 mL of trifluoroacetic acid and 1 mL of dichloromethane was stirred for 0.75 h. Flash chromatography (silica gel, 100% ethyl acetate, 1% ammonia) afforded 7.5 mg (52%) of the title compound as a glass: $^1$H NMR (400 MHz, CD$_3$OD) δ7.96 (d, 1H, J=8.5 Hz), 7.56 (m, 1H), 7.55 (s, 1H), 7.07 (d, 2H, J=8.6 Hz), 7.02 (d, 2H, J=8.6 Hz), 6.49 (s, 1H), 6.14 (s, 1H), 4.82 (m, 1H), 4.06 (t, 2H, J=8.7 Hz), 3.23 (t, 2H, J=8.7 Hz), 2.96–2.60 (m, 8H), 2.23 (s, 3H), 1.69 (m, 2H), 1.45–1.20 (m, 10H), 0.88 (m, 3H).

EXAMPLE 17

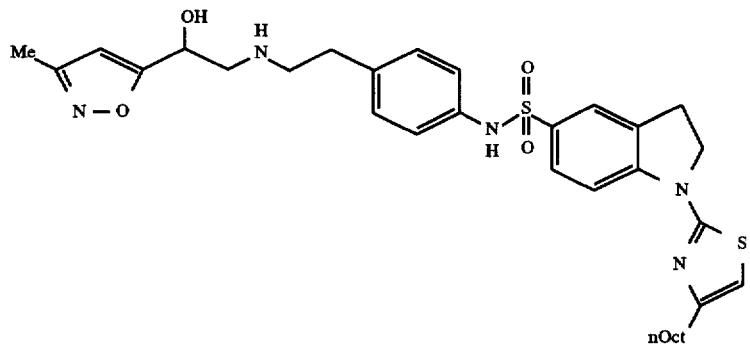

N-[4-[2-[[2-Hydroxy-2-methylisoxazol-5-yl)ethyl]amino]ethyl]phenyl]-1-(4-octylthiazol-2-yl)-5-indolinesulfonamide

EXAMPLE 18

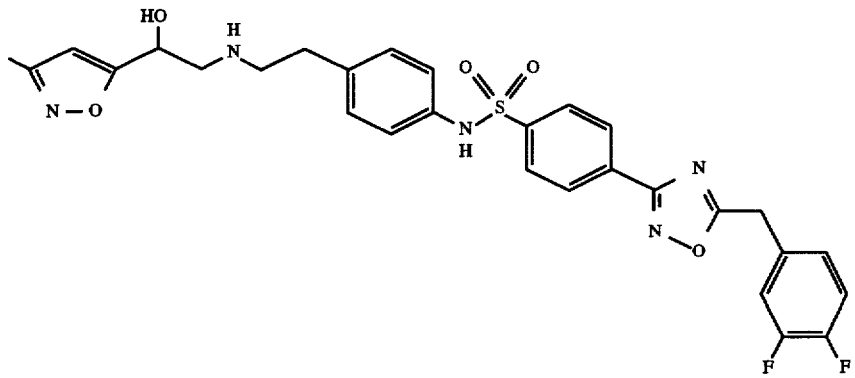

N-[4-[2-[[2-Hydroxy-2-(3-methylisoxazol-5-yl)ethyl]amino]ethyl]phenyl]-4-[5(3,4-difluorophenylmethyl)-[1,2,4]-oxadiazol-3-yl]benzenesulfonamide A suspension of 12.3 mg (0.0715 mmol) of 3,4-difluorophenyl acetic acid and 13.7 mg (0.0715 mmol) of 1-(3-dimethylaminopropyl)-3-ethylcarbodiimide hydrochloride in 2.0 mL of diglyme was stirred for 5 min, and 40.0 mg (0.0715 mmol) of N-[4-[2-[N-(1,1-dimethylethoxycarbonyl)-N-[2-hydroxy-2-(3-methylisoxazol-5-yl)ethyl]amino]ethyl]phenyl]-4-(aminooximidomethyl)benzenesulfonamide (prepared from the product from Example 15 according to the procedure outlined in Example 63, steps A and B) was added. After stirring for 14 h, the reaction was heated at 100° C. for 2 h. The diglyme was removed in vacuo. Flash chromatography (silica gel, 30–50% ethyl acetate-hexanes) afforded 19.0 mg (38%) of the Boc-protected title compound as a colorless glass.

A solution of 19.0 mg (0.0268 mmol) of the Boc-protected title compound in 300 μL of trifluoroacetic acid and 300 μL of dichloromethane was stirred for 0.5 h. The volatile components were removed in vacuo. Flash chromatography (silica gel, 3% (10% ammonia-methanol)-dichloromethane) afforded 10.2 mg (64%) of the title compound: $^1$H NMR (500 MHz, CD$_3$OD) δ8.10 (d, 2H, J=8.4 Hz), 7.82 (d, 2H, J=8.4 Hz), 7.36–7.31 (m, 1H), 7.27–7.17 (m, 2H, 7.09 (d, 2H, J=8.3 Hz), 7.01 (d, 2H, J=8.3 Hz), 6.15 (s, 1H), 4.82 (m, 1H), 4.36 (s, 2H), 2.93–2.68 (m, 6H), 2.72 (s, 3H).

Following the procedures outlined for Examples 11–18, the compounds listed in Table 2 were prepared.

TABLE 2

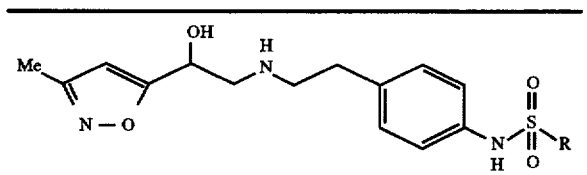

| Example | R | Selected $^1$H NMR (CD$_3$OD) Data |
|---|---|---|
| 19 | 4-(hexylaminocarbonylamino)phenyl | 7.57(d, 2H, J=8.9Hz), 7.43(d, 2H, J=8.9Hz), 3.16(t, 2H, J=7.0 Hz), 1.50(m, 2H), 1.32(m, 6H), 0.90(m, 3H). |
| 20 | 4-(3-octyl-2-imidazolidinon-1-yl)phenyl | 7.63(m, 4H), 3.83(m, 2H), 3.52 (m, 2H), 3.25(m, 2H), 1.56(m, 2H), 1.33(m, 10H), 0.88(m, 3H). |
| 21 | 4-[4-(3-cyclopentylpropyl)-5-tetrazolon-1-yl]phenyl | (CDCl$_3$ instead of CD$_3$OD) 8.12(d, 2H, J=8.7Hz), 7.87(d, 2H, J=8.7 Hz), 4.02(t, 2H, J=7.3Hz), 1.89 (m, 2H), 1.79(m, 2H), 1.61(m, 2H), 1.53(m, 2H), 1.40(m, 2H), 1.27(m, 1H), 1.09(m, 2H). |
| 22 | 4-(4-octyl-5-tetrazolon-1-yl)phenyl | 1.86–1.59(m, 2H), 1.35–1.25(m, 10H), 0.86(t, 3H, J=6.8Hz). |
| 23 | 4-[5-(3,4,5-trifluorobenzyl)-[1,2,4]-oxadiazol-3-yl]phenyl | 7.24–7.20(m, 2H), 4.38(s, 2H), 3.18–3.01(m, 4H), 2.85–2.80(m, 2H). |
| 24 | 4-[5-[1-(4-fluorophenyl)-1-methoxymethyl]-[1,2,4]-oxadiazol-3-yl]phenyl | 7.56–7.52(m, 2H), 7.16–7.12(m, 2H), 5.77(s, 1H), 3.47(s, 3H), 2.92–2.70(m, 6H). |
| 25 | 1-(6-hexylpyrid-2-yl)indolin-5-yl | 7.59–7.56(m, 1H), 6.76(m, 1H), 6.65(m, 1H), 2.91–2.70(m, 8H), 1.78–1.75(m, 2H), 1.35–1.32(m, 6H), 0.89(t, 3H, J=7.1Hz). |
| 26 | 1-[6-(3-cyclopentylpropyl)pyrid-2-yl]indolin-5-yl | 1.84–1.75(m, 6H), 1.61–1.51(m, 3H), 1.38–1.34(m, 2H), 1.10–1.06 |

TABLE 2-continued

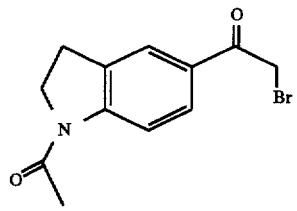

| Example | R | Selected $^1$H NMR (CD$_3$OD) Data |
|---|---|---|
| 27 | 1-(6-octylpyrid-2-yl)indolin-5-yl | (m, 2H). 2.92(m, 2H), 2.75(t, 2H, J=7.6 Hz), 1.77(m, 2H), 1.34–1.27(m, 10H), 0.89–0.86(m, 3H). |
| 28 | 4-(5-pentyl-[1,2,4]-oxadiazol-3-yl)phenyl | 3.00–2.90(m, 4H), 1.86–1.83(m, 2H), 1.41–1.38(m, 4H), 0.92–0.91 (m, 3H). |
| 29 | 4-(5-heptyl-[1,2,4]-oxadiazol-3-yl)phenyl | 2.96–2.71(m, 6H), 1.83–1.81(m, 2H), 1.39–1.29(m, 8H), 0.88–0.87 (m, 3H). |

EXAMPLE 30

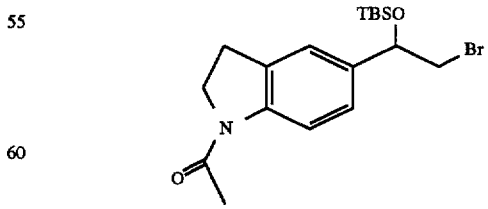

1-Acetyl-5-(bromoacetyl)indoline

To a stirred mixture of 12.1 g (90.5 mmol) of aluminum chloride in 26 mL of 1,2-dichloroethane at 10° C. was added 3.24 mL (37.2 mmol) of bromoacetyl bromide in one portion. The resultant mixture was stirred at 10° C. for 20 minutes, then a solution of 5 g (31 mmol) of 1-acetylindoline in 20 mL of 1,2-dichloroethane was added from a dropping funnel over a period of 15 minutes. When the addition was complete, the mixture was stirred at 50° C. for 1 h, then cooled to 15° C. and added to a mixture of 65 g of ice and 65 g of water making sure the temperature remained below 20° C. The mixture was stirred at ambient temperature for 2 h then filtered and the wet solid washed with water until the last aqueous wash was pH 5. The solid was then washed with hexane and dried at 50° C. under vacuum overnight to provide 6.7 g (77%) of the title compound as an off-white solid: $^1$H NMR (400MHz, CDCl$_3$) δ8.24 (d, 1H, J=8.42 Hz), 7.83 (m, 2H), 4.40, (s, 2H), 4.13 (t, 2H, J=8.6 Hz), 3.24 (t, 2H, J=8.6 Hz), 2.25 (s, 3H).

EXAMPLE 31

1-Acetyl-α-(bromomethyl)-5-indolinemethanol, dimethyl-1,1-dimethylethylsilyl ether To a suspension of 2.04 g (7.23 mmol) of bromoketone from Example 30 in 40 mL methanol at 0° C. was added 275 mg (7.23 mmol) of sodium borohydride in several portions. The resultant mixture was stirred at ambient temperature for 1 h, then 40 mL of water was added and stirring continued for 20 minutes. The mixture was extracted with two portions of dichloromethane, and the combined organic phases washed with one portion each of water and brine, dried over magnesium sulfate, and concentrated to give 1.65 g (5.8 mmol) of the resultant alcohol as a pale green solid. The alcohol was protected without further purification by combining with 1.31 g (8.7 mmol) of tert-butyldimethylsilyl chloride and 2.0 g (29.4 mmol) of imidazole in 25 mL of N,N-dimethylformamide. After stirring at ambient temperature for 4.5 h the mixture was poured into water and extracted with four portions of ethyl ether. The combined organic phases were washed with one portion each of water and brine, dried over magnesium sulfate, and concentrated. Purification by flash column chromatography (silica gel, 50% ethyl acetate/hexane) gave 790 mg (27% overall yield) of the title compound as a white solid: $^1$H NMR (400 MHz, CDCl$_3$) δ8.13 (d, 1H, J=8.1 Hz), 7.12, (m, 2H), 4.77(dd, J=7.73, 4.43 Hz), 4.05 (t, 2H, J=8.46 Hz), 3.39 (m, 2H), 3.18 (t, 2H, J=8.46 Hz), 2.20 (s, 3H), 0.86 (s, 9H), 0.08 (s, 3H), −0.09 (s, 3H).

EXAMPLE 32

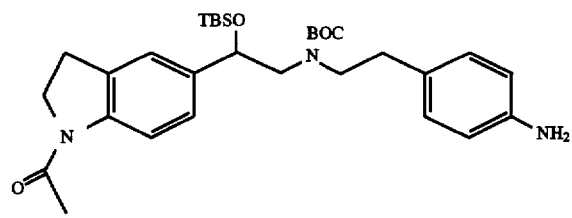

N-[2-[4-(Aminophenyl)]ethyl]-2-[(dimethyl-1,1-dimethylethylsilyl)oxy]-2-(1-acetyl-5-indolinyl) ethylcarbamic acid 1,1-dimethylethyl ester To a solution of 750 mg (1.88 mmol) of the product from Example 31 in 15 mL of acetonitrile was added 705 mg (4.7 mmol) of sodium iodide, 1.3 mL (7.46 mmol) of N,N-diisopropylethylamine, and 762 mg (3.76 mmol) of 4-nitrophenethylamine hydrochloride. The mixture was heated at reflux in a sealed tube for 20 h then concentrated in vacuo. Purification by flash column chromatography (silica gel, 2% methanol/0.2% ammonium hydroxide/ dichloromethane) provided 675 mg (74%) of the secondary amine as a brown oil. This product was dissolved in 20 mL of dichloromethane, and 390 mg (1.8 mmol) of di-tert-butyl dicarbonate was added. After stirring for 4 hours at ambient temperature the solvent was removed in vacuo and the residue purified by flash column chromatography (silica gel, 50% ethyl acetate/hexane) to give 712 mg (87%) of the protected amine as a dark brown oil. The resultant carbonate in 15 mL methanol was stirred over palladium hydroxide on carbon under an atmosphere of hydrogen for 6 h. The solution was filtered through celite, the filtrate concentrated, and the residue purified by flash column chromatography (silica gel, 2% methanol/0.2% ammonium hydroxide/ methylene chloride) to give 400 mg (60%) of the title compound: $^1$H NMR (400 MHz, CD$_3$OD, mixture of rotamers) δ8.02 (d, 1H, J=8.3 Hz), 7.1 (m, 2H), 6.88 (m, 2H,) 6.65 (d, 2H, J=7 Hz), 4.85 (m, 1H), 4.12 (t, 2H, J=8.5) 3.5–2.95 (m, 6H), 2.6 (t, 2H, J=7 Hz), 2.2 (s, 3H), 1.44 (s, 4.9H), 1.42 (s, 4.1H), 0.85 (s, 9H), 0 (s, 3H), −0.14 (s, 1.7H), −0.15 (s, 1.3H).

EXAMPLE 33

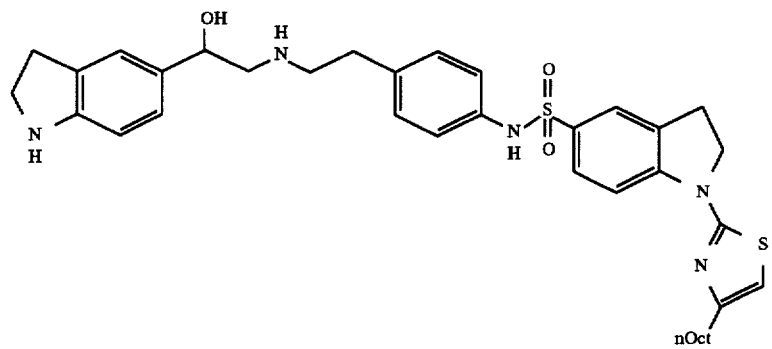

N-[4-[2-[[2-Hydroxy-2-(5-indolinyl)ethyl]amino]ethyl] phenyl]-1-(4-octylthiazol-2-yl)-5-indolinesulfonamide To a solution of 80 mg (0.144 mmol) of the product from Example 32 in 2 mL of dichloromethane at 0° C. was added 50 μL (0.62 mmol) of pyridine, followed by 60 mg (0.145 mmol) of 1-(4-octylthiazol-2-yl)-5-indolinesulfonyl chloride from Example 16 as a solution in 2 mL of dichloromethane. The resultant mixture was stirred overnight at ambient temperature then concentrated in vacuo and purified by preparative TLC (silica gel, 5% methanol/0.5% ammonium hydroxide/methylene chloride) to give 113 mg (84%) of the sulfonamide. A portion of the sulfonamide (62 mg, 0.067 mmol) was taken up in 2 mL of 2N hydrochloric acid and acetonitrile was added to effect dissolution. The mixture was heated at 60° C. overnight then concentrated and purified by preparative TLC (silica gel, 10% methanol/1.0% ammonium hydroxide/methylene chloride) to provide 10 mg (22%) of the title compound: $^1$H NMR (400 MHz, CD$_3$OD) δ7.8 (d, 1H, J=8 Hz), 7.55(m, 2H), 7.0 (m, 5H), 6.9(d, 1H, J=8 Hz), 6.6 (d, 1H, J=8 Hz), 6.49 (s, 1H), 4.6 (dd, 1H, J=8.0, 6.4 Hz), 4.05 (t, 2H, J=8 Hz), 3.45 (t, 2H, J=8 Hz), 3.22 (t, 2H, J=8 Hz), 2.95 (t, 2H, J=8 Hz), 2.85–2.65 (m, 6H), 2.63 (t, 2H, J=8 Hz), 1.7 (m, 2H), 1.33 (m, 10H), 0.89 (t, 3H, J=7.2 Hz).

EXAMPLE 34

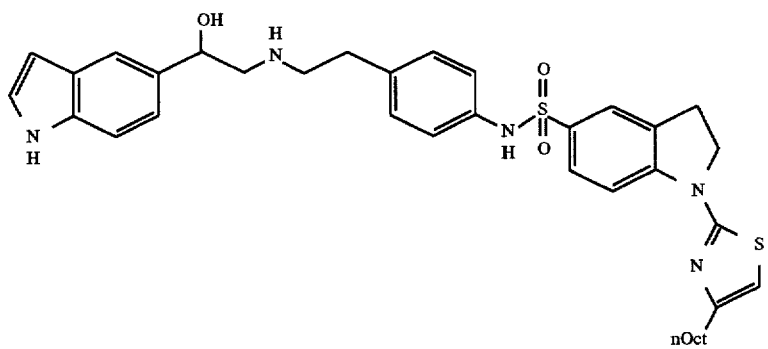

N-[4-[2-[[2-Hydroxy-2-(5-indolyl)ethyl]amino]ethyl]phenyl]-1-(4-octylthiazol-2-yl)-5-indolinesulfonamide To a mixture of 10 mg (0.015 mmol) of the product from Example 33 in 2 mL of freshly distilled tetrahydrofuran was added 13 mg (0.15 mmol) activated manganese dioxide. The resultant mixture was stirred at ambient temperature overnight then filtered through Celite. The Celite was washed with methanol to ensure complete recovery of product from the manganese dioxide. The filtrate was concentrated in vacuo and purified by preparative TLC (silica gel, 10% methanol/ethyl acetate) to afford 3.4 mg (34%) of the title compound: $^1$H NMR (400 MHz, CD$_3$OD) δ7.98 (d, 1H, J=8 Hz), 7.55 (d, 1H, J=8 Hz), 7.5 (d, 2H, J=8 Hz), 7.21 (d, 1H, J=4 Hz), 7.02 (m, 5H), 6.48 (s, 1H), 6.4 (d, 1H, J=4 Hz), 4.8 (dd, 1H, J=8, 4 Hz), 4.05 (t, 2H, J=8 Hz), 3.22 (t, 2H, J=8 Hz), 2.85 (m, 4H), 2.72 (m, 2H), 2.62 (t, 2H, J=8 Hz) 1.7 (m, 2H), 1.3 (m, 10H), 0.88 (t, 3H, J=7.2 Hz).

EXAMPLE 35

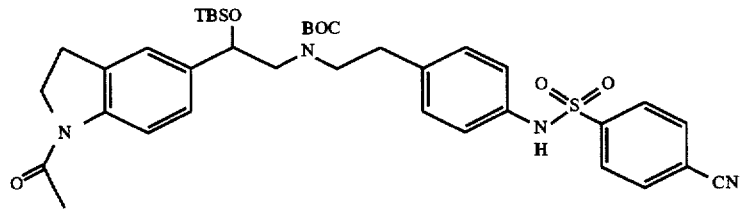

N-[4-[2-[N-(1,1-Dimethylethoxycarbonyl)-N-[2-[(dimethyl-1,1-dimethylethyl-silyl)oxy]-2-(1-acetyl-5-indolinyl)ethyl]amino]ethyl]phenyl]-4-cyanobenzenesulfonamide To a solution of 200 mg (0.36 mmol) of the product from Example 32 in 4 mL of dichloromethane at 0° C. was added 80 μL (0.99 mmol) of pyridine, followed by 88 mg (0.44 mmol) of 4-cyanobenzenesulfonyl chloride. The mixture was stirred at ambient temperature for 48 h then concentrated in vacuo. Purification by preparative TLC (silica gel, 5% methanol/dichloromethane) provided 214 mg (83%) of the title compound: $^1$H NMR (400 MHz, CD$_3$OD) δ8.03 (m, 1H), 7.78 (d, 2H, J=8 Hz), 7.68 (d, 2H, J=8 Hz), 7.2–6.94 (m, 6H), 4.85 (m, 1H), 4.12 (t, 2H, J=8 Hz), 3.55–2.85 (m, 6H), 2.68 (t, 2H, J=7 Hz), 2.22 (s, 3H), 1.44 (s, 4.5H), 1.39 (s, 4.5H), 0.88 (s, 9H), 0 (s, 3H), −0.13 (s, 1.7H), −0.15 (s, 1.3H).

EXAMPLE 36

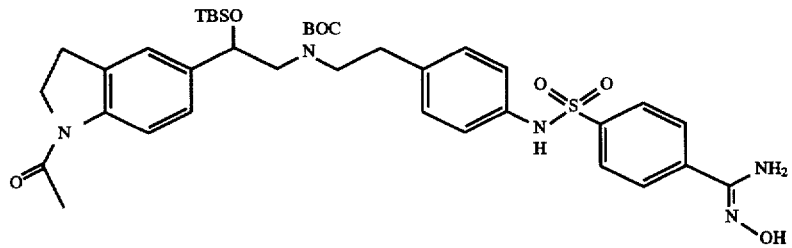

N-[4-[2-[N-(1,1-Dimethylethoxycarbonyl)-N-[2-[(dimethyl-1,1-dimethylethyl-silyl)oxy]-2-(1-acetyl-5-indolinyl)ethyl]amino]ethyl]phenyl]4-(aminooximidomethyl)benzenesulfonamide The cyano derivative from Example 35 was converted to the title compound following the procedure outlined in Example 63, Step B with one change: the reaction mixture was heated at reflux for six hours instead of overnight. Purification by flash column chromatography (silica gel, 5% methanol/0.5% ammonium hydroxide/methylene chloride) provided the title compound in 91% yield: $^1$H NMR (400 MHz, CD$_3$OD, mixture of rotamers) δ8.02 (d, 1H, J=8 Hz), 7.65 (m, 4H), 7.2–7.0 (m, 2H), 6.9 (m, 4H), 4.85 (m, 1H), 4.12 (t, 2H, J=8 Hz), 3.55–2.9 (m, 6H), 2.68, (m, 2H), 2.2 (s, 3H), 1.42 (s, 4.2H), 1.38 (s, 4.8H), 0.88 (s, 9H), 0 (s, 3H), −0.13 (s, 1.6H), −0.16 (s, 1.4H).

EXAMPLE 37

N-[4-[2-[[2-Hydroxy-2-(5-indolyl)ethyl]amino]ethyl]phenyl]-4-(5-pentyl-[1,2,4]-oxadiazol-3-yl)benzenesulfonamide The title compound was prepared from the compound in Example 37 following the procedure outlined in Example 34 in 25% yield after purification by preparative TLC (silica gel, 10% methanol/20% ethyl acetate/70% methylene chloride): $^1$H NMR (400 MHz, CD$_3$OD) δ8.1 (d, 2H, J=8 Hz), 7.82 (d, 2H, J=8 Hz), 7.53 (s, 1H), 7.35 (d, 1H, J=8 Hz), 7.23 (d, 1H, J=4 Hz), 7.1–7.0 (m, 5H), 6.4 (d, 1H, J=4 Hz), 4.84 (m, 1H) 3.0–2.85 (m, 6H), 2.76 (t, 2H, J=8 Hz), 1.83 (m, 2H), 1.38 (m, 4H), 0.93 (m, 3H).

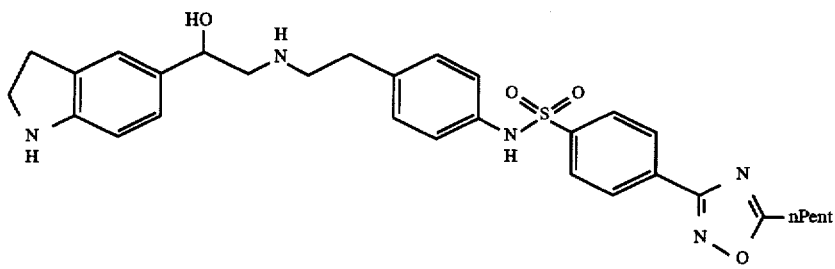

N-[4-[2-[[2-Hydroxy-2-(5-indolinyl)ethyl]amino]ethyl]phenyl]-4-(5-pentyl-[1,2,4]-oxadiazol-3-yl)benzenesulfonamide To a solution of 97 mg (0.129 mmol) of the product from Example 36 in 10 mL of 2-methoxyethyl ether was added 25 mg (0.129 mmol) of [1-ethyl-3-(dimethylaminopropyl)-carbodiimide] hydrochloride (EDC) and 16 µL (0.129 mmol) of hexanoic acid, and the resultant mixture stirred overnight at ambient temperature. TLC (silica gel, 10% methanol/1% ammonium hydroxide/methylene chloride) indicated the reaction was incomplete so an additional 25 mg of EDC and 16 µL of hexanoic acid were added and stirring continued for an additional 24 h at ambient temperature. The mixture was then heated at 120° C. for 4 h, concentrated in vacuo, and purified by flash colum chromatography (silica gel, 3% methanol/0.3% ammonium hydroxide/methylene chloride). The resultant 61 mg of oxadiazole was taken up in 4 mL of 2N hydrochloric acid and acetonitrile added until completely dissolved. This mixture was heated at 60° C. overnight, then concentrated and purified by preparative TLC (silica gel, 8% methanol/0.8% ammonium hydroxide/methylene chloride) to provide 35 mg of the title compound in 43% overall yield: $^1$H NMR (400 MHz, CD$_3$OD) δ8.11 (d, 2H, J=8 Hz), 7.83 (d, 2H, J=8 Hz), 7.08–6.9 (m, 6H), 6.6 (d, 1H, J=8 Hz), 4.61 (m, 1H), 3.45 (t, 2H, J=8 Hz), 3.0–2.9 (m, 4H), 2.86–2.7 (m, 6H), 1.85 (m, 2H), 1.4 (m, 4H), 0.95 (m, 3H).

EXAMPLE 38

Following the procedures outlined for Examples 30–38, the compounds listed in Table 3 were prepared.

TABLE 3

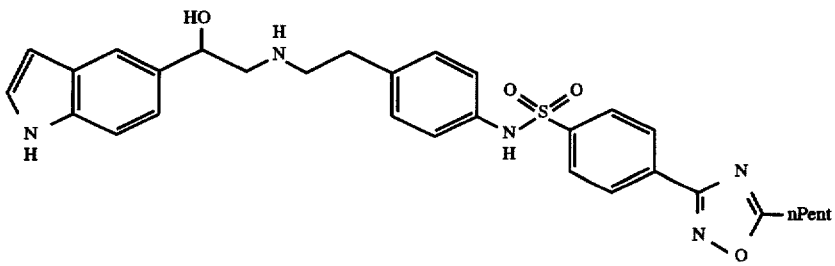

| Example | R | Selected $^1$H NMR (CD$_3$OD) Data |
|---|---|---|
| 39 | 4-(hexylaminocarbonylamino)phenyl | 7.57(d, 2H, J=8Hz), 7.42(d, 2H, J=8Hz), 3.15(t, 2H, J=7Hz), 1.5 (m, 2H), 1.32 (m, 6H), 0.9 (t, 3H, J=7Hz) |
| 40 | 4-(3-octyl-2-imidazolidinon-1-yl)phenyl | 7.62(m, 4H), 3.8(m, 2H), 3.5(m, 2H), 3.24(t, 2H, J=8Hz), 1.55(m, 2H), 1.3 (m, 10H), 0.9(t, 3H, J=8 Hz) |
| 41 | 4-(3-hexyl-2-imidazolon-1-yl)phenyl | 7.78 (apparent s, 4H) 6.9(d, 1H, J=4Hz), 6.7(d, 1H, J=4Hz) 3.63(t, 2H, J=8Hz), 1.68(m, 2H), 1.3(m, 6H), 0.9(t, 3H, J=8Hz) |
| 42 | 4[4-(3-cyclopentylpropyl)-5-tetrazolon-1-yl]phenyl | 8.05(d, 2H, J=8Hz), 7.85(d, 2H, J=8Hz), 3.98(t, 2H, J=8Hz), 1.8 (m, 6H), 1.55(m, 4H), 1.38(m, 2H), 1.1(m, 1H) |
| 43 | 4-[5-(3,4-dilfuorobenzyl)-[1,2,4]- | 8.1(d, 2H, J=8Hz), 7.8(d, 2H, J=8 Hz), 7.3(m, 1H), 7.2(m, 1H), 7.15 |

TABLE 3-continued

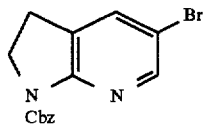

| Example | R | Selected ¹H NMR (CD₃OD) Data |
|---|---|---|
| 44 | 1-[6-(3-cyclopentylpropyl)pyrid-2-yl]indolin-5-yl oxadiazol-3-yl]phenyl | (m, 1H), 4.34(s 2H) 8.38(d, 1H, J=8Hz), 7.5 (m, 2H), 7.05(M, 1H), 6.75(d, 1H, J=8Hz), 6.64(d, 1H, J=8Hz), 4.03(t, 2H, J=8Hz), 3.15(t, 2H, J=8Hz), 2.7 (t, 2H, J=8Hz), 1.8 (m, 6H), 1.55 (m, 4H), 1.35(m, 2H), 1.1(m, 1H) |
| 45 | 1-(6-octylpyrid-2-yl)indolin-5-yl | 8.35(d, 1H, J=8Hz), 7.5(m, 2H), 7.04(M, 1H), 6.71(d, 1H, J=8Hz), 6.6(d, 1H, J=8Hz), 3.98(t, 2H, J=8 Hz), 3.14(t, 2H, J=8Hz), 2.7(t, 2H, J=8Hz), 1.75(m, 2H), 1.3(m, 10H), 0.87(t, 3H, J=8Hz) |

EXAMPLE 46

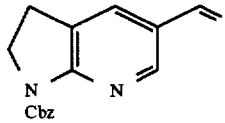

7-Aza-5-bromo-1-[(phenylmethoxy)carbonyl]indoline

To a stirred suspension of 990 mg (5 mmol) of 7-aza-5-bromoindoline in 30 mL of a 2M aqueous sodium carbonate solution was added 1.9 mL (13.3 mmol) of benzoyl chloride at 0° C. The reaction mixture was stirred for 1 h, before dilution with ethyl acetate (100 mL). The solution was washed with saturated aqueous sodium bicarbonate solution (2×20 mL), water (30 mL), back extracted with ethyl acetate (2×30 mL), washed with brine (20 mL), dried over magnesium sulfate, and concentrated. Purification by flash chromatography (silica gel, 33% ethyl acetate/hexane) gave 1.09 g of the title compound: ¹H NMR (400 MHz, CDCl₃) δ8.26 (d, 1H, J=2 Hz), 7.50 (d, 1H, J=2 Hz), 7.45–7.27 (m, 5H), 5.30 (s, 2H), 4.10–4.05 (m, 2H), 3.10–3.03 (m, 2H).

EXAMPLE 47

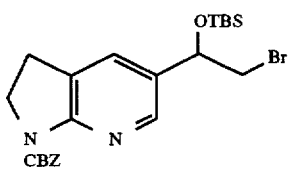

7-Aza-1-(phenylmethoxy)carbonyl-5-vinylindoline

A 200 mg (0.6 mmol) portion of the compound from Example 46 was dissolved in 1.5 mL of toluene, and vinyltributyltin (263 μL, 0.9 mmol) and tetrakis(triphenylphosphine)palladium (13.8 mg, 0.012 mmol) were added and the solution was heated under reflux for 2 h. Upon cooling, ether (10 mL) and potassium fluoride solution (10 mL) were added and stirring was continued for 20 min, followed by dilution with ether (20 mL), and water (20 mL). The layers were separated, the aqueous phase back extracted with ether (3×10 mL), the organic phase washed with brine (10 mL), dried with magnesium sulfate, and concentrated. Purification by flash chromatography (silica gel, 33% ethyl acetate/hexane) yielded 146.7 mg (56.6% over 2 steps) of the title compound: ¹H NMR (CDCl₃) δ8.20 (s, 1H), 7.53 (s, 1H), 7.47–7.43 (m, 2H), 7.36–7.27 (m, 3H), 6.63 (dd, 1H, J=16.8+10.4 Hz), 5.64 (d,1H, J=16.8 Hz), 5.31 (s,2H), 5.21 (d, 1H, J=10.4 Hz), 4.08 (t, 2H, J=8 Hz), 3.06 (t, 2H, J=8 Hz).

EXAMPLE 48

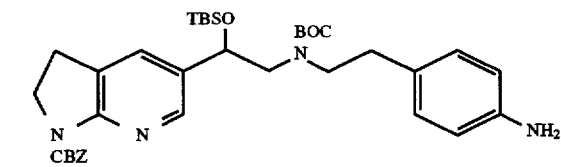

7-Aza-α-(bromomethyl)-1-(phenylmethoxy)carbonyl-5-indolinemethanol, dimethyl-1,1-dimethylethylsilyl ether Hydrogen bromide was bubbled into a solution of 318 mg (1.136 mmol) of the compound from Example 47 in methanol (20 mL) at 0° C. for 2 min. Stirring was continued for 10 min, followed by concentration to give the hydrobromide salt (400 mg) which was dissolved in water (9 mL)/tetrahydrofuran (4.5 mL). N-Bromosuccinimide (207.7 mg, 1.17 mmol) was added and stirring was continued for 10 min before dilution with water (20 mL), and extraction with chloroform (4×20 mL). The organic phase was dried with magnesium sulfate and concentrated to give 447 mg crude alcohol, which was dissolved in N,N-dimethylformamide (5 mL). tert-Butyldimethylsilylchloride (251 mg, 1.665 mmol) and imidazole (378 mg, 5.55 mmol) were added and stirring was continued for 4 h when a further 200 mg (1.33 mmol) tert-butyldimethylsilylchloride was added and stirring continued for 16 h. The reaction was diluted with ether (20 mL) and water (20 mL). After separation the aqueous phase was extracted with ether (2×20 mL), the combined organic phase was washed with water (10 mL), brine (10 mL), dried with magnesium sulfate, and concentrated. Purification by flash chromatography (silica gel, 25% ethyl acetate/hexane) yielded 314 mg (56% overall yield) of the title compound: ¹H NMR (CDCl₃) δ8.17 (s, 1H), 7.48–7.41 (m, 3H), 7.38–7.26 (m, 3H), 5.30 (s, 2H), 4.80 (dd, 1H, J=6+4 Hz), 4.08 (t, 2H, J=8 Hz), 3.46–3.32 (m, 2H), 3.08 (t, 2H, J=8 Hz), 0.86 (s, 9H), 0.09 (s, 3H), –0.9 (s, 3H).

EXAMPLE 49

N-[2-[4-(Aminophenyl)]ethyl]-2-[(dimethyl-1,1-dimethylethylsilyl)oxy]-2-[7-aza-1-(phenylmethoxy)carbonyl-5-indolinyl]ethylcarbamic acid 1,1-dimethylethyl ester To a solution of 150 mg (0.306 mmol) of bromide from Example 48 in 2.4 mL of acetonitrile was added 114.7 mg (0.765 mmol) of sodium iodide, 0.213 mL (1.224 mmol) of N,N-diisopropylethylamine, and 124 mg (0.612 mmol) of 4-nitrophenethylamine hydrochloride. The mixture was heated at 110° C. in a sealed tube for 20 h, cooled, diluted with methanol (10 mL), filtered through celite, then concentrated in vacuo. Purification by flash column chromatography (silica gel, 2% methanol/0.2% ammonium hydroxide/ dichloromethane) provided 121 mg (68%) of the secondary amine as a brown oil. This product was dissolved in 3.5 mL of dichloromethane and 55.6 mg (0.252 mmol) di-tert-butyl dicarbonate was added. After stirring for 2 hours at ambient temperature the solvent was removed in vacuo and the residue purified by flash column chromatography (silica gel, 2% methanol/dichloromethane) to give 118.6 mg (84%) of the protected amine as a dark brown oil. A portion of the resultant carbonate (15 mg, 0.022 mmol), hydrazine hydrate (2.6 µL), and raney nickel in 0.5 mL of methanol was heated under reflux for 10 min, cooled, diluted with methanol (5 mL), filtered through celite, and concentrated to give 13 mg (90%) of the title compound which was not purified further: $^1$H NMR (400 MHz, CD$_3$OD, mixture of rotamers) ∂8.03 (s, 0.5H), 7.96 (s, 0.5H), 7.56 (s, 0.5H), 7.49 (s, 0.5H), 7.47–7.28 (m, 5H), 6.92–6.85 (m, 2H), 6.68–6.63 (m, 2H), 5.29 (s,2H),4.99–4.83 (m, 1H), 4.08 (t, 2H, J=8 Hz), 3.53–3.03 (m, 6H), 2.66–2.60 (m, 2H), 1.4 (s, 9H), 0.88 (s, 9H), 0.04 (s, 3H), –0.91 (s, 1.5H), –0.90 (s, 1.5H).

compound: $^1$H NMR (400 MHz, CD$_3$OD) ∂7.66–7.59 (m, 4H), 7.57 (s, 1H), 7.28 (s, 1H), 7.08–6.97 (m, 4H), 4.59–4.54 (m, 1H), 3.86–3.80 (m, 2H), 3.58 (t, 2H, J=8 Hz), 3.52–3.48 (m, 2H), 3.25 (t, 2H, J=7.2 Hz), 3.01 (t, 2H, J=8 Hz), 2.90–2.67 (m, 6H), 1.60–1.50 (m, 2H), 1.36–1.23 (10H), 0.91–0.85 (m, 3H).

EXAMPLE 50

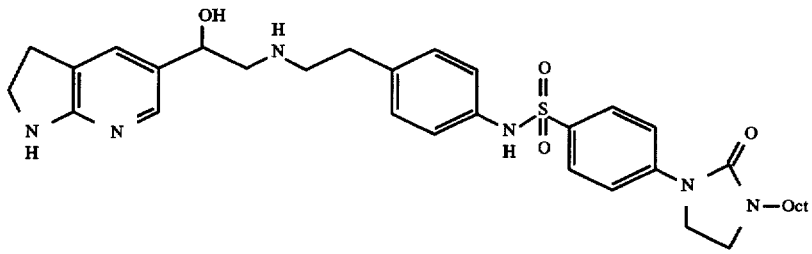

N-[4-[2-[[2-(7-Aza-5-indolinyl)-2-hydroxyethyl]amino] ethyl]phenyl]-4-(3-octyl-2-imidazolidinon-1-yl) benzenesulfonamide To a solution of 13 mg (0.019 mmol) of the aniline from Example 49 in 1 mL dichloromethane at 0° C. was added 6.2 µL pyridine, followed by 8.6 mg (0.023 mmol) of 4-(3-octyl-2-imidazolidinon-1-yl)benzensulfonyl chloride from Example 6. The resultant mixture was stirred overnight at ambient temperature then concentrated in vacuo and purified by preparative TLC (silica gel, 3% methanol/methylene chloride) to give 17.4 mg (93%) of the sulfonamide. This was dissolved in 2 mi methanol, and stirred with Pd(OH)$_2$ under a hydrogen atmosphere for 2 h, dilution with methanol (10 mL), filtration through celite, and concentration yielded the free indoline (13 mg, 87%). This was taken up in 1 mL of 2N hydrochloric acid and acetonitrile added until a clear solution was obtained. The mixture was heated at 60° C. overnight then concentrated and purified by preparative TLC (silica gel, 10% methanol/1.0% ammonium hydroxide/ methylene chloride) to provide 5 mg (66%) of the title

EXAMPLE 51

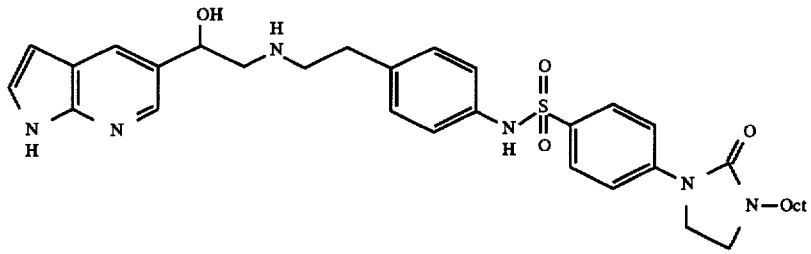

N-[4-[2-[[2-(7-Aza-5-indolyl)-2-hydroxyethyl]amino]ethyl] phenyl]-4-(3-octyl-2-imidazolidinon-1-yl) benzenesulfonamide To a mixture of 5 mg (7.9 µmol) of the above indoline from Example 50 in 1 told of fleshly distilled tetrahydrofuran was added 6.8 mg (7.9 mmol) of activated manganese dioxide. The resultant mixture was stirred at ambient temperature overnight then filtered through celite which was washed with methanol to ensure complete recovery of product from the manganese dioxide. The filtrate was concentrated in vacuo and purified by preparative TLC (silica gel, 10% methanol/1.0% ammonium hydroxide/methylene chloride) to afford 2.6 mg (52%) of the title compound: $^1$H NMR, (400 MHz, CD$_3$OD) ∂8.16 (d,1H, J=2 Hz), 7.95 (d,1H, J=2 Hz), 7.66–7.59 (m, 4H), 7.38 (d, 1H, J=3 Hz), 7.08–6.98 (m, 4H), 6.47 (d, 1H, J=3 Hz), 4.90–4.85 (m, 1H) 3.85–3.78 (m, 2H), 3.53–3.47 (m, 2H), 3.22 (t, 2H, J=8 Hz), 2.9–2.69 (m, 6H), 1.60–1.50 (m, 2H), 1.37–1.23 (10H), 0.91–0.85 (m, 3H).

EXAMPLE 52

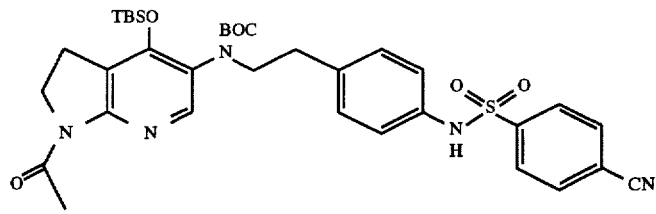

N-[4-[2-[N-(1,1-Dimethylethoxycarbonyl)-N-[2-hydroxy-2-(1-acetyl-7-aza-5-indolinyl)ethyl]amino]ethyl]phenyl]-4-cyanobenzenesulfonamide To 131.25 mg (0.225 mmol) of N-[2-[4-(aminophenyl)]ethyl]-2-[(dimethyl-1,1-dimethylethyl-silyl)oxy]-2-(1-acetyl-7-aza-5-indolinyl)ethylcarbamic acid 1,1-dimethylethyl ester (prepared from 1-acetyl-7-aza-5-bromoindoline following the procedures outlined in Examples 47–49) in 3 mL dichloromethane at 0° C. was added 72 µL (0.9 mmol) pyridine, followed by 54.4 mg (0.27 mmol) of 4-cyanobenzene-sulfonyl chloride. The resultant mixture was stirred overnight at ambient temperature then concentrated in vacuo and purified by preparative TLC (silica gel, 2% methanol/0.2% ammonium hydroxide/methylene chloride) to give 136.6 mg (84%) of the title compound. $^1$H NMR, (400 MHz, CD$_3$OD) ∂8.05 (s, 0.5H), 7.99 (s, 0.5H), 7.82–7.75 (m, 4H), 7.58 (s, 0.5H), 7.52 (s, 0.5H), 7.06–6.95 (m, 4H), 4.98–4.93 (m, 1H), 4.09–4.00 (m, 2H), 3.60–2.97 (m, 6H), 2.71 (t, 2H, J=7.2 Hz), 2.63 (s, 3H), 1.36 s (4.5H), 1.35 (s, 4.5H), 0.86 (s, 9H), 0.03 (s, 3H), −0.90 (s, −1.5H), −0.89 (s, 1.5H).

EXAMPLE 53

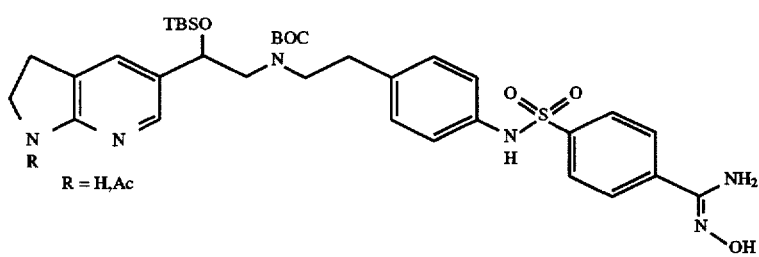

N-[4-[2-[N-(1,1-Dimethylethoxycarbonyl)-N-[2-[(dimethyl-1,1-dimethylethyl-silyl)oxy]-2-(1-acetyl-7-aza-5-indolinyl)ethyl]amino]ethyl]phenyl]-4-(aminooximidomethyl)benzenesulfonamide and N-[4-[2-[N-(1,1-dimethylethoxycarbonyl)-N-[2-[(dimethyl-1,1-dimethylethyl-silyl)oxy]-2-(7-aza-5-indolinyl)ethyl]amino]ethyl]phenyl]-4-(aminooximidomethyl)benzenesulfonamide The cyano derivative from Example 52 was converted to the title compound following the procedure outlined in Example 63, Step B with one change: the reaction mixture was heated at reflux for six hours instead of overnight. Purification by preparative TLC (silica gel, 10% methanol/1% ammonium hydroxide/methylene chloride) provided the 1-acetyl derivative accompanied by the free indoline as a 2/1 mixture (129 mg, 90% combined yield).

EXAMPLE 54

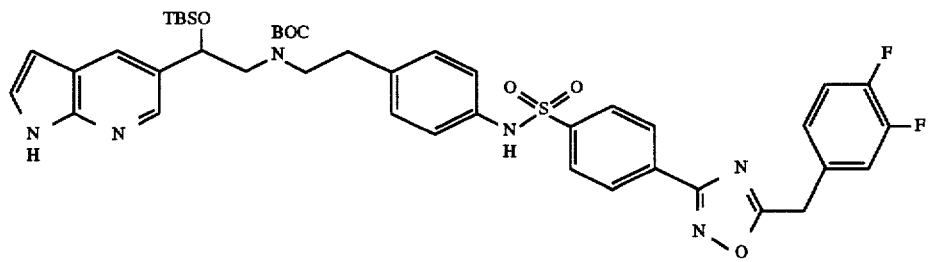

N-[4-[2-[N-(1,1-Dimethylethoxycarbonyl)-N-[2-[(dimethyl-1,1-dimethylethyl-silyl)oxy]-2-(7-aza-5-indolyl)ethyl]amino]ethyl]phenyl]-4-[5-(3,4-difluorophenylmethyl)-[1,2,4]-oxadiazol-3-yl]benzenesulfonamide To a solution of 129 mg (0.18 mmol) of the mixture from Example 53 in 5 mL of 2-methoxyethyl ether was added 41.4 mg (0.216 mmol) of [1-ethyl-3-(dimethylaminopropyl)-carbodiimide] hydrochloride (EDC) and 37.2 mg (0.216 mmol) of 3,4-diflurophenylacetic acid, and the resultant mixture stirred overnight at ambient temperature. The mixture was then heated at 120° C. for 5 h to effect cyclization of the oxadiazole ring which occurred with partial oxidation of the indoline. Concentration in vacuo, and purification of the mixture by preparative TLC (silica gel, 10% methanol/1% ammonium hydroxide/methylene chloride) yielded the title compound 15.7 mg (10%): ¹H NMR (400 MHz, CD₃OD) δ8.18–8.03 (m,3H), 7.93 (s, 0.5H), 7.86 (s, 0.5H), 7.80–7.74 (m,2H), 7.39–7.16 (m, 4H), 7.03–6.96 (m, 4H), 6.46 (d, 1H, J=4 Hz), 5.11–4.95 (m, 1H), 4.38 (s, 2H), 3.52–2.58 (m,6H), 1.30 (s, 4.5H), 1.21 (s, 4.5H), 0.85–0.78 (m, 9H), –0.99 (s, 3H), –0.83 (s, 1.5H), –0.82 (s, 1.5H).

EXAMPLE 55

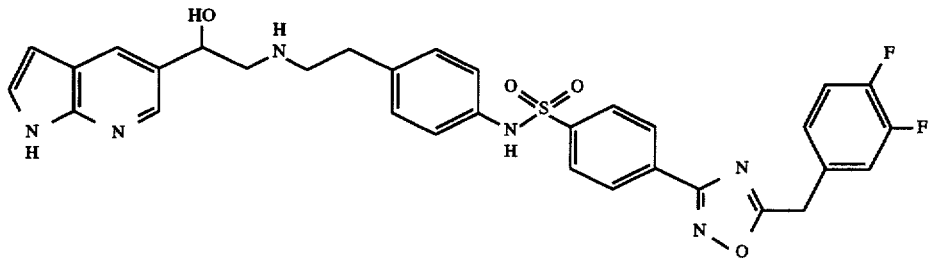

N-[4-[2-[[2-Hydroxy-2-(7-aza-5-indolyl)ethyl]amino]ethyl]phenyl]-4-[5-(3,4-difluorophenylmethyl)-[1,2,4]-oxadiazol-3-yl]benzenesulfonamide The indole derivative from Example 54 (15.7 mg, 0.0185 mmol) was taken up in 1 mL of 2N hydrochloric acid and acetonitrile added until completely dissolved. This mixture was heated at 60° C. overnight, then concentrated and purified by preparative TLC (silica gel, 10% methanol/1% ammonium hydroxide/methylene chloride) to provide 11.4 mg (97% yield) of the title compound: ¹H NMR (400 MHz, CD₃OD) δ8.17 (s, 1H), 8.11 (d, 2H, J=8 Hz), 7.96 (s, 1H), 7.82 (d, 2H, J=8 Hz), 7.38 (d, 2H, J=4 Hz), 7.36–7.13 (m, 3H), 7.07–6.96 (m, 4H), 6.46 (d, 2H, J=4 Hz), 4.90–4.83 (m, 1H), 4.33 (s, 2H), 2.91–2.70 (m, 6H).

Following analogous procedures outlined for Examples 46–55 starting with N-Boc, N-Cbz and N-acetate protected indolines, the compounds listed in Table 4 were prepared.

TABLE 10

| Example | R | Selected ¹H NMR (CD₃OD) Data |
|---|---|---|
| 56 | 4-(hexylaminocarbonylamino)phenyl | 7.58(d, 2H, J=8Hz), 7.42(d, 2H, J=8Hz), 3.13(t, 2H, J=7.2Hz), 1.51–1.42(m, 2H), 1.38–1.25(6H), 0.91–0.86(m, 3H). |
| 57 | 1-(4-octylthiazol-2-yl)indolin-5-yl | 7.98(d, 1H, J=8Hz), 7.56(d, 1H, J=8Hz), 7.51(s, 1H), 6.48(s, 1H), 4.08(t, 2H, J=9.6Hz), 3.24(t, 2H, J=9.6Hz), 2.12(t, 2H, J=8Hz), 1.72–1.65(m, 2H), 1.38–1.22(10H), 0.90–0.85(m, 3H) |
| 58 | 4-(3-hexyl-2-imidazolon-1-yl)phenyl | 7.51 (apparent s, 4H), 6.92(d, 1H, J=2.5Hz), 6.68(d, 1H, J=2.5Hz), |

TABLE 10-continued

| Example | R | Selected ¹H NMR (CD₃OD) Data |
|---|---|---|
| | | 3.61(t, 2H, J=7.2Hz), 1.71–1.63(m, 2H), 1.36–1.27(m, 6H), 0.92–0.86 (m, 3H) |

EXAMPLE 59

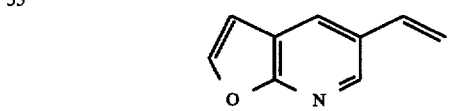

5-Vinylfuro[2,3-b]pyridine

To o-iodoxybenzoic acid (1.036g, 3.7 mmol) in dimethyl sulfoxide (7.4 mL) was added furo[2,3-b]pyridine-5-methanol (500 mg, 3.36 mmol). Stirring was continued for 2.5 h before the addition of water, filtration, and extraction of the filtrate with ethyl ether (3×30 mL). The organic phase was washed with brine (10 mL), dried with magnesium sulfate, and concentrated. Purification by flash chromatography (silica gel, 25% ethyl acetate/hexane) yielded 5-formyl-furo[2,3-b]pyridine (270 mg, 55%). This material (260 mg, 1.77 mmol) in toluene/tetra-hydrofuran (2 mL each) was added at −78° C. to a solution of methyltriphenylphosphorane (2.12 mmol) in toluene (15 mL). Stirring was continued at this temperature for 15 min, followed by warming to 20° C. over 1 h. Dilution with ethyl ether was followed by filtration through celite, and concentration. Purification by flash chromatography (silica gel, 25% ethyl acetate/hexane) yielded 241.5 mg (94% yield) of the title compound as a colorless oil: $^1$H NMR (CDCl$_3$) ∂8.32 (d,1H, J=2 Hz), 7.97 (d, 1H, J=2 Hz), 7.68 (d,1H, J=2 Hz), 6.80 (dd, 1H, J=18+12 Hz), 6.76 (d, 1H, J=2 Hz), 5.79 (d,1H, J=18 Hz), 5.32 (d, 1H, J=12 Hz).

EXAMPLE 60

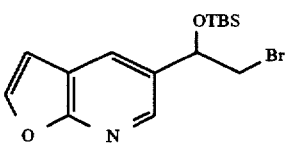

α-(Bromomethyl)-5-furo[2,3-b]pyridinemethanol, dimethyl-1,1-dimethylethylsilyl ether The olefin from Example 59 (230 mg, 1.58 mmol) was dissolved in water (9 mL)/tetrahydrofuran (4.5 mL). N-Bromosuccinimide (291 mg, 1.634 mmol) was added and stirring was continued for 30 min before dilution with water (20 mL), and extraction with chloroform (4×20 mL). The organic phase was dried with magnesium sulfate and concentrated to give 401 mg crude alcohol, which was dissolved in N,N-dimethylformamide (5 mL). tert-Butyldimethylsilylchloride (251 mg, 1.665 mmol) and imidazole (374 mg, 5.5 mmol) were added and stirring was continued for 4 h when a further 100 mg (0.67 mmol) tert-butyldimethylsilylchloride was added and stirring continued for 16 h. The reaction was diluted with ether (20 mL) and water (20 mL). After separation the aqueous phase was extracted with ether (2×20 mL), the combined organic phase was washed with water (10 mL), brine (10 mL), dried with magnesium sulfate, and concentrated. Purification by flash chromatography (silica gel, 17% ethyl acetate/hexane) yielded 380 mg (68% overall yield) of the title compound: $^1$H NMR (CD$_3$OD) ∂8.30 (s, 1H), 8.13 (s, 1H), 7.92 (d,1H, J=2 Hz), 6.95 (d,1H, J=2 Hz),5.15 (t, 1H, J=6.4 Hz), 3.61 (d, 2H, J=6.4 Hz), 0.91 (s, 9H), 0.16 (s, 3H), −0.92 (s, 3H).

EXAMPLE 61

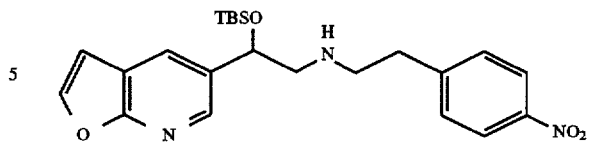

N-[2-[4-(Nitrophenyl)]ethyl]-2-[(dimethyl-1,1-dimethylethyl-silyl)oxy]-2-[5-furo[2,3-b]pyridinyl]ethylamine To a solution of 377 mg (1.06 mmol) of bromide from Example 60 in 8.5 mL acetonitrile was added 398 mg (2.65 mmol) of sodium iodide, 0.74 mL (4.24 mmol) of N,N-diisopropylethylamine, and 430 mg (2.12 mmol) of 4-nitrophenethylamine hydrochloride. The mixture was heated at 110° C. in a sealed tube for 20 h, cooled, diluted with methanol (20 ml), filtered through celite, then concentrated in vacuo. Purification by flash column chromatography (silica gel, 2% methanol/dichloromethane) provided 380 mg (81%) of the secondary amine as an oil: $^1$H NMR (CD$_3$OD) ∂8.23 (d,1H, J=2 Hz), 8.13 (d, 2H, J=10 Hz), 8.05 (d,1H, J=2 Hz), 7.89 (d,1H, J=2.5 Hz), 7.45 (d, 2H, J=10 Hz), 6.92 (d,1H, J=2.5 Hz), 5.01–4.96 (m, 1H), 2.97–2.75 (m, 6H), 0.79 (s, 9H), 0.02 (s, 3H), −0.80 (s, 3H).

EXAMPLE 62

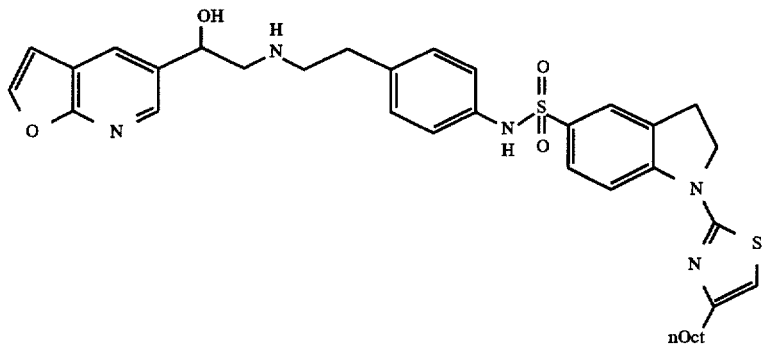

N-[4-[2-[[2-Hydroxy-2-(5-furo[2,3-b]pyridinyl)ethyl]amino]ethyl]phenyl]-1-(4-octylthiazol-2-yl)-5-indolinesulfonamide The amine (380 mg, 0.86 mmol) from Example 61 was dissolved in 10 mL of dichloromethane and 212.6 mg (0.975 mmol) of di-tert-butyl dicarbonate was added. After stirring for 16 hours at ambient temperature the solvent was removed in vacuo to give 447.6 mg of crude protected amine. This was dissolved in 10 mL of methanol and was stirred over palladium hydroxide on carbon under an atmosphere of hydrogen for 3 h. The solution was filtered through celite, the filtrate concentrated, and the residue purified by flash column chromatography (silica gel, 1–2% methanol/methylene chloride) to give 57 mg (13%) of the desired aniline accompanied by 300 mg of the dihydrofuran analog. To the former (57 mg, 0.112 mmol) in 1 mL dichloromethane at 0° C. was added 32 µL pyridine, followed by 57 mg (0.138 mmol) of 1-(4-octylthiazol-2-yl)-5-indolinesulfonyl chloride from Example 140. The resultant mixture was stirred overnight at ambient temperature then concentrated in vacuo and purified by preparative TLC (silica gel, 5% methanol/methylene chloride) to give 56 mg of a mixture containing the desired sulfonamide. This was taken up in 2 mL of 2N hydrochloric acid and acetonitrile added until a clear solution was obtained. The mixture was heated at 60° C. for 1 h then concentrated and purified twice by preparative TLC (silica gel, 10% methanol/1.0% ammonium hydroxide/methylene chloride) to yield 10 mg of the title compound: $^1$H NMR (400 MHz, CD$_3$OD) δ8.21 (d,1H, J=2 Hz), 8.04 (d,1H, J=2 Hz), 7.97 (d,1H, J=9 Hz), 7.88 (d,1H, J=2.5 Hz), 7.57 (d,1H, J=9 Hz), 7.53 (s, 1H), 7.08–6.99 (m, 4H), 6.90 (d, 1H, J=2.5 Hz), 6.49 (s, 1H), 4.91–4.85 (m, 1H), 4.06 (t, 2H, J=9.6 Hz), 3.23 (t, 2H, J=9.6 Hz), 2.90–2.58 (m, 8H), 1.72–1.63 (m, 2H), 1.38–1.20 (m, 10H), 0.91–0.85 (m, 3H).

EXAMPLE 63

A. Preparation of (R)-N-[4-[2-[N-(1,1-dimethylethoxycarbonyl)-N-[2-hydroxy-2-(pyridin-3-yl)ethyl]amino]ethyl]phenyl]-4-cyanobenzensulfonamide To a solution of 780 mg (2.18 mmol) of (R)-N-[2-[4-(aminophenyl)]ethyl]-2-hydroxy-2-(pyrid-3-yl)ethylcarbamic acid 1,1-dimethylethyl ester (see WO95/29159 published 2 Nov. 1995) in 10 mL of methylene chloride was added 0.16 mL of pyridine and 450 mg of 4-cyanobenzenesulfonyl chloride. The reaction mixture was stirred at room temperature overnight. TLC (acetone 25%, methylene chloride 75%) on silica gel indicated the formation of a major fast moving (rf 0.48) spot. Purification by flash chromatography (silica gel, 25% acetone/dichloromethane) gave 716 mg of the title compound as a white solid: $^1$H NMR (400 MHz, CDCl$_3$) δ8.53–8.44 (m, 2H), 7.78 (d, J=8.7 Hz, 2H), 7.72–7.68 (m, 1H), 7.67 (d, J=8.7 Hz, 2H), 7.3–7.23 (m, 1H), 7.1–6.9 (m, 4H), 4.8 (m, 1H), 3.5–2.6 (m, 6H), 1.42 (s, 9H).

B. Preparation of (R)-N-[4-[2-[N-(1,1-dimethylethoxycarbonyl)-N-[2-hydroxy-2-(pyridin-3-yl)ethyl]amino]ethyl]phenyl]-4-(aminooximidomethyl)benzensulfonamide The cyano compound from Step A (250 mg), 175 mg of hydroxylamine hydrochloride, and 414 mg of finely ground potassium carbonate were suspended in 10 mL of ethanol and heated at reflux overnight. TLC (acetone/methylene chloride 40:60) indicated the formation of a new low rf product (rf 0.18). The mixture was filtered. The filtrate was concentrated to give the title compound, which was used without further purification: $^1$H NMR (400 MHz, CDCl$_3$) δ8.42–8.35 (m, 2H), 7.62 (m, 1H), 7.54 (s, 4H), 7.18 (m, 1H), 6.95–6.8 (m, 4H), 5.03 (br s, 2H), 4.73 (m, 1H), 3.25–3.0 (m, 4H), 2.6–2.5 (m, 2H), 1.30 (s, 9H).

EXAMPLE 64

N-[4-[2-[[2-Hydroxy-2-[5-(2,3-dihydrofuro[2,3-b]pyridin)yl]ethyl]amino]ethyl]phenyl]1-(4-octylthiazol-2-yl)-5-indolinesulfonamide To the dihydrofuran biproduct from Example 62 (38.3 mg, 0.0746 mmol) in 1 mL dichloromethane at 0° C. was added 32 μL pyridine, followed by 37 mg (0.089 mmol) of 1-(4-octylthiazol-2-yl)-5-indolinesulfonyl chloride from Example 140. The resultant mixture was stirred overnight at ambient temperature then concentrated in vacuo and purified by preparative TLC (silica gel, 5% methanol/methylene chloride) to give 46.8 mg of the desired sulfonamide. This was taken up in 2 mL of 2N hydrochloric acid and acetonitrile added until a clear solution was obtained. The mixture was heated at 60° C. for 2 h then concentrated and purified by preparative TLC (silica gel, 10% methanol/1.0% ammonium hydroxide/methylene chloride) to yield 21.8 mg of the title compound: $^1$H NMR (400 MHz, CD$_3$OD) 7.97 (d,1H, J=8 Hz), 7.78 (s,1H), 7.60–7.50 (m, 3H), 7.08–6.99 (m, 4H), 6.50 (s, 1H), 4.68–4.59 (m, 3H), 4.08 (t, 2H, J=9.6 Hz), 3.30–3.19 (m, 4H), 2.87–2.60 (m, 8H), 1.80–1.71 (m, 2H), 1.43–1.28 (m, 10H), 0.97–0.91 (m, 3H).

What is claimed is:

1. A compound having the formula I:

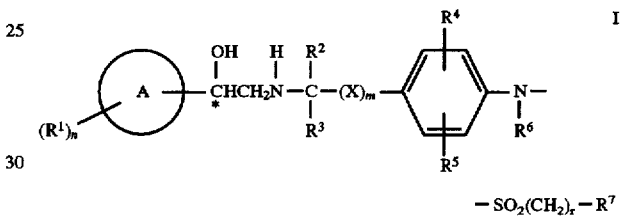

$$-SO_2(CH_2)_r-R^7$$

where
n is 0 to 5;
m is 0 or 1;
r is 0 to 3;
A is
(1) a 5 or 6-membered heterocyclic ring with from 1 to 4 heteroatoms selected from oxygen, sulfur and nitrogen, excluding pyridyl,
(2) a benzene ring fused to a 5 or 6-membered heterocyclic ring with from 1 to 4 heteroatoms selected from oxygen, sulfur and nitrogen, or
(3) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen;

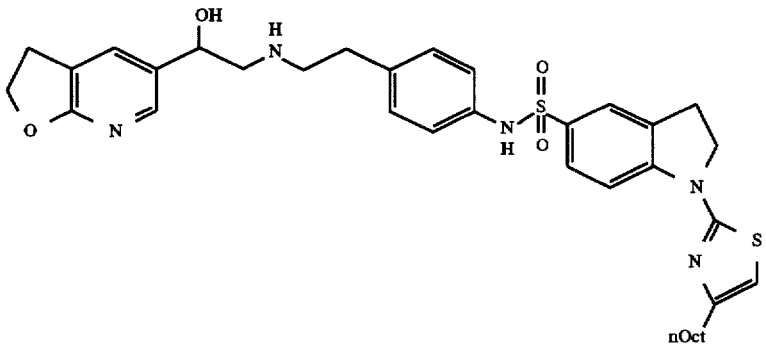

$R^1$ is
(1) hydroxy,
(2) oxo,
(3) halogen,
(4) cyano,
(5) $NR^8R^8$,
(6) $SR^8$,
(7) trifluoromethyl,
(8) $C_1$–$C_{10}$ alkyl,
(9) $OR^8$,
(10) $S(O)_tR^9$, where t is 1 or 2,
(11) $OCOR^9$,
(12) $NR^8COR^9$,
(13) $COR^9$,
(14) $NR^8SO_2R^9$,
(15) $NR^8CO_2R^8$, or
(16) $C_1$–$C_{10}$ alkyl substituted by hydroxy, halogen, cyano, $NR^8R^8$, $SR^8$, trifluoromethyl, $OR^8$, $C_3$–$C_8$ cycloalkyl, phenyl, $NR^8COR^9$, $COR^9$, $S(O)_tR^9$, where t is 1 or 2, $OCOR^9$, $NR^8SO_2R^9$ or $NR^8CO_2R^8$;

$R^2$ and $R^3$ are independently
(1) hydrogen,
(2) $C_1$–$C_{10}$ alkyl or
(3) $C_1$–$C_{10}$ alkyl with 1 to 5 substituents selected from hydroxy, $C_1$–$C_{10}$ alkoxy, and halogen;

X is
(1) —$CH_2$—,
(2) —$CH_2$—$CH_2$—,
(3) —CH=CH— or
(4) —$CH_2O$—;

$R^4$ and $R^5$ are independently
(1) hydrogen,
(2) $C_1$–$C_{10}$ alkyl,
(3) halogen,
(4) $NHR^8$,
(5) $OR^8$
(6) $S(O)_tR^9$, where t is 1 or 2, or
(7) $NHSO_2R^9$;

$R^6$ is
(1) hydrogen or
(2) $C_1$–$C_{10}$ alkyl;

$R^7$ is Z-$(R^{1a})_n$;

$R^{1a}$ is
(1) $R^1$,
(2) $C_3$–$C_8$ cycloalkyl,
(3) phenyl optionally substituted with up to 4 groups independently selected from $R^8$, $NR^8R^8$, $OR^8$, $S(O)_tR^8$ where t is 0 to 2 and halogen, or
(4) 5 or 6-membered heterocycle with from 1 to 4 heteroatoms selected from oxygen, sulfur and nitrogen, optionally substituted with up to four groups independently selected from oxo, $R^8$, $NR^8R^8$, $OR^8$, $S(O)_tR^8$ where t is 0 to 2, and halogen;

Z is
(1) phenyl,
(2) naphthyl,
(3) a 5 or 6-membered heterocyclic ring with from 1 to 4 heteroatoms selected from oxygen, sulfur and nitrogen,
(4) a benzene ring fused to a $C_5$–$C_{10}$ carbocyclic ring,
(5) a benzene ring fused to a 5 or 6-membered heterocyclic ring with from 1 to 4 heteroatoms selected from oxygen, sulfur and nitrogen,
(6) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen, or
(7) a 5 or 6-membered heterocyclic ring with from 1 to 4 heteroatoms selected from oxygen, sulfur and nitrogen fused to a $C_5$–$C_{10}$ carbocyclic ring;

$R^8$ is
(1) hydrogen,
(2) $C_1$–$C_{10}$ alkyl,
(3) $C_3$–$C_8$ cycloalkyl,
(4) Z optionally having 1 to 5 substituents selected from halogen, nitro, oxo, $NR^{10}R^{10}$, $C_1$–$C_{10}$ alkyl, $C_1$–$C_{10}$ alkoxy, $C_1$–$C_{10}$ alkylthio, and $C_1$–$C_{10}$ alkyl having 1 to 5 substituents selected from hydroxy, halogen, $CO_2H$, $CO_2$—$C_1$–$C_{10}$ alkyl, $SO_2$—$C_1$–$C_{10}$ alkyl, $C_3$–$C_8$ cycloalkyl, $C_1$–$C_{10}$ alkoxy, and Z optionally substituted by from 1 to 3 of halogen, $C_1$–$C_{10}$ alkyl or $C_1$–$C_{10}$ alkoxy, or
(5) $C_1$–$C_{10}$ alkyl having 1 to 5 substituents selected from hydroxy, halogen, $CO_2H$, $CO_2$—$C_1$–$C_{10}$ alkyl, $SO_2$—$C_1$–$C_{10}$ alkyl, $C_3$–$C_8$ cycloalkyl, $C_1$–$C_{10}$ alkoxy, $C_1$–$C_{10}$ alkyl, and Z optionally substituted by from 1 to 5 of halogen, trifluoromethyl, trifluoromethoxy, $C_1$–$C_{10}$ alkyl or $C_1$–$C_{10}$ alkoxy;

$R^9$ is
(1) $R^8$ or
(2) $NR^8R^8$;

$R^{10}$ is
(1) $C_1$–$C_{10}$ alkyl, or
(2) two $R^{10}$ groups together with the N to which they are attached formed a 5 or 6-membered ring optionally substituted with $C_1$–$C_{10}$ alkyl; or a pharmaceutically acceptable salt thereof.

2. A compound of claim 1 where n is 0 to 3;

m is 1;

r is 0 to 2;

X is —$CH_2$—;

$R^1$ is
(1) hydroxy,
(2) halogen,
(3) cyano,
(4) trifluoromethyl,
(5) $NR^8R^8$,
(6) $NR^8SO_2R^9$,
(7) $NR^8COR^9$,
(8) $NR^8CO_2R^8$, or
(9) $C_1$–$C_{10}$ alkyl optionally substituted by hydroxy;

$R^2$, $R^3$ are independently
(1) hydrogen or
(2) methyl;

$R^4$, $R^5$ and $R^6$ are each hydrogen;

$R^7$ is Z—$(R^{1a})_n$; and when $R^1$ is part of the definition of $R^{1a}$ it has the meaning defined in claim 1.

3. A compound of claim 2 wherein:

A is selected from the group consisting of thiazolyl, isoxazolyl, indolinyl, indolyl, furopyridyl, tetrahydrofuropyridyl, 7-azaindolyl and 7-azaindolinyl;

r is 0;

$R^2$ and $R^3$ are each H;

$R^7$ is Z—$(R^{1a})_n$;

Z is phenyl or indolinyl;

$R^{1a}$ is
(1) halogen
(2) $NR^8COR^9$, or (3) a 5- or 6-membered heterocycle with from 1 to 4 heteroatoms selected from oxygen, sulfur and nitrogen, optionally substituted with up to four groups independently selected from oxo, and $R^8$;

$R^8$ is
(1) hydrogen
(2) $C_1$–$C_{10}$alkyl
(3) $C_1$–$C_{10}$alkyl having 1 to 5 substituents selected from hydroxy, halogen, $C_3$–$C_8$ cycloalkyl, $C_1$–$C_{10}$ alkoxy, and Z optionally substituted by from 1 to 5 of halogen, trifluoromethyl, trifluoromethoxy, $C_1$–$C_{10}$ alkyl or $C_1$–$C_{10}$ alkoxy; and $R^9$ is $NR^8R^8$.

4. A compound of claim 1 selected from the group consisting of:

N-[4-[2-[[2-Hydroxy-2-(thiazol-5-yl)ethyl]amino]ethyl] phenyl]-4-(3-octyl-2-imidazolidinon-1-yl) benzenesulfonamide;

N-[4-[2-[[2-Hydroxy-2-(thiazol-5-yl)ethyl]amino]ethyl] phenyl]-4-(hexylaminocarbonylamino) benzenesulfonamide;

N-[4-[2-[[2-Hydroxy-2-(thiazol-5-yl)ethyl]amino]ethyl] phenyl]-4-(4-iodo)benzenesulfonamide;

N-[4-[2-[[2-Hydroxy-2-(3-methylisoxazol-5-yl)ethyl] amino]ethyl]phenyl]-1-(4-octylthiazol-2-yl)-5-indolinesulfonamide;

N-[4-[2-[[2-Hydroxy-2-(3-methylisoxazol-5-yl)ethyl] amino]ethyl]phenyl]-4-[5-(3,4-difluorophenylmethyl)-[1,2,4]-oxadiazol-3-yl]benzenesulfonamide;

N-[4-[2-[[2-Hydroxy-2-(3-methylisoxazol-5-yl)ethyl] amino]ethyl]phenyl]-4-(hexylaminocarbonylamino) benzenesulfonamide;

N-[4-[2-[[2-Hydroxy-2-(3-methylisoxazol-5-yl)ethyl] amino]ethyl]phenyl]-4-(3-octyl-2-imidazolidinon-1-yl) benzenesulfonamide;

N-[4-[2-[[2-Hydroxy-2-(3-methylisoxazol-5-yl)ethyl] amino]ethyl]phenyl]-4-[4-(3-cyclopentylpropyl)-5-tetrazolon-1-yl]benzenesulfonamide;

N-[4-[2-[[2-Hydroxy-2-(3-methylisoxazol-5-yl)ethyl] amino]ethyl]phenyl]-4-(4-octyl-5-tetrazolon-1-yl) benzenesulfonamide;

N-[4-[2-[[2-Hydroxy-2-(3-methylisoxazol-5-yl)ethyl] amino]ethyl]phenyl]-4-[5-(3,4,5-trifluorobenzyl)-[1,2,4]-oxadiazol-3-yl]benzenesulfonamide;

N-[4-[2-[[2-Hydroxy-2-(3-methylisoxazol-5-yl)ethyl] amino]ethyl]phenyl]-4-[5-[1-(4-fluorophenyl)-1-methoxymethyl]-[1,2,4]-oxadiazol-3-yl] benzenesulfonamide;

N-[4-[2-[[2-Hydroxy-2-(3-methylisoxazol-5-yl)ethyl] amino]ethyl]phenyl]-1-(6-hexylpyrid-2-yl)-5-indolinesulfonamide;

N-[4-[2-[[2-Hydroxy-2-(3-methylisoxazol-5-yl)ethyl] amino]ethyl]phenyl]-1-[6-(3-cyclopentylpropyl)pyrid-2-yl]-5-indolinesulfonamide;

N-[4-[2-[[2-Hydroxy-2-(3-methylisoxazol-5-yl)ethyl] amino]ethyl]phenyl]-1-(6-octylpyrid-2-yl)-5-indolinesulfonamide;

N-[4-[2-[[2-Hydroxy-2-(3-methylisoxazol-5-yl)ethyl] amino]ethyl]phenyl]-4-(5-pentyl-[1,2,4]-oxadiazol-3-yl) benzenesulfonamide;

N-[4-[2-[[2-Hydroxy-2-(3-methylisoxazol-5-yl)ethyl] amino]ethyl]phenyl]-4-(5-heptyl-[1,2,4]-oxadiazol-3-yl) benzenesulfonamide;

N-[4-[2-[[2-Hydroxy-2-(5-indolinyl)ethyl]amino]ethyl] phenyl]-1-(4-octylthiazol-2-yl)-5-indolinesulfonamide;

N-[4-[2-[[2-Hydroxy-2-(5-indolyl)ethyl]amino]ethyl] phenyl]-1-(4-octylthiazol-2-yl)-5-indolinesulfonamide;

N-[4-[2-[[2-Hydroxy-2-(5-indolinyl)ethyl]amino]ethyl] phenyl]-4-(5-pentyl-[1,2,4]-oxadiazol-3-yl) benzenesulfonamide;

N-[4-[2-[[2-Hydroxy-2-(5-indolyl)ethyl]amino]ethyl] phenyl]-4-(5-pentyl-[1,2,4]-oxadiazol-3-yl) benzenesulfonamide;

N-[4-[2-[[2-Hydroxy-2-(5-indolyl)ethyl]amino]ethyl] phenyl]-4-(hexylaminocarbonylamino) benzenesulfonamide;

N-[4-[2-[[2-Hydroxy-2-(5-indolyl)ethyl]amino]ethyl] phenyl]-4-(3-octyl-2-imidazolidinon-1-yl) benzenesulfonamide;

N-[4-[2-[[2-Hydroxy-2-(5-indolyl)ethyl]amino]ethyl] phenyl]-4-(3-hexyl-2-imidazolon-1-yl) benzenesulfonamide;

N-[4-[2-[[2-Hydroxy-2-(5-indolyl)ethyl]amino]ethyl] phenyl]-4-[4-(3-cyclopentylpropyl)-5-tetrazolon-1-yl] benzenesulfonamide;

N-[4-[2-[[2-Hydroxy-2-(5-indolyl)ethyl]amino]ethyl] phenyl]-4-[5-(3,4-difluorobenzyl)-[1,2,4]-oxadiazol-3-yl]benzenesulfonamide;

N-[4-[2-[[2-Hydroxy-2-(5-indolyl)ethyl]amino]ethyl] phenyl]-1-[6-(3-cyclopentylpropyl)pyrid-2-yl]-5-indolinesulfonamide;

N-[4-[2-[[2-Hydroxy-2-(5-indolyl)ethyl]amino]ethyl] phenyl]-1-(6-octylpyrid-2-yl)-5-indolinesulfonamide;

N-[4-[2-[[2-(7-Aza-5-indolinyl)-2-hydroxyethyl]amino] ethyl]phenyl]-4-(3-octyl-2-imidazolidinon-1-yl) benzenesulfonamide;

N-[4-[2-[[2-(7-Aza-5-indolyl)-2-hydroxyethyl]amino]ethyl] phenyl]4(3-octyl-2-imidazolidinon-1-yl) benzenesulfonamide;

N-[4-[2-[[2-Hydroxy-2-(7-aza-5-indolyl)ethyl]amino]ethyl] phenyl]-4-[5-(3,4-difluorophenylmethyl)-[1,2,4]-oxadiazol-3-yl]benzenesulfonamide;

N-[4-[2-[[2-Hydroxy-2-(7-aza-5-indolyl)ethyl]amino]ethyl] phenyl]4-(hexylaminocarbonylamino) benzenesulfonamide;

N-[4-[2-[[2-Hydroxy-2-(7-aza-5-indolyl)ethyl]amino]ethyl] phenyl]4-(3-hexyl-2-imidazolon-1-yl) benzenesulfonamide;

N-[4-[2-[[2-Hydroxy-2-(7-aza-5-indolyl)ethyl]amino]ethyl] phenyl]-1-(4-octylthiazol-2-yl)-5-indolinesulfonamide;

N-[4-[2-[[2-Hydroxy-2-(5-furo[2,3-b]pyridinyl)ethyl] amino]ethyl]phenyl]-1-(4-octylthiazol-2-yl)-5-indolinesulfonamide;

N-[4-[2-[[2-Hydroxy-2-[5-(2,3-dihydrofuro[2,3-b]pyridin) yl]ethyl]amino]ethyl]phenyl]-1-(4-octylthiazol-2-yl)-5-indolinesulfonamide.

5. A compound of claim 1 with the structural formula Ic:

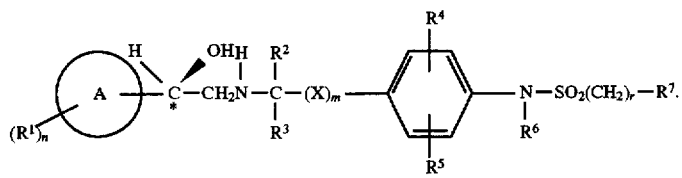

6. A method for the treatment of diabetes which comprises administering to a diabetic patient an effective amount of a compound of claim 1.

7. A method for the treatment of obesity which comprises administering to an obese patient an effective amount of a compound of claim 1.

8. A method for lowering triglyceride levels and cholesterol levels or raising high density lipoprotein levels which comprises administering to a patient needing lower triglyceride and cholesterol levels or higher high density lipoprotein levels an effective amount of a compound of claim 1.

9. A method for decreasing gut motility which comprises administering to a patient in need of decreased gut motility, an effective amount of a compound of claim 1.

10. A method for reducing neurogenic inflammation of airways which comprises administering to a patient in need of reduced neurogenic inflammation, an effective amount of a compound of claim 1.

11. A method for reducing depression which comprises administering to a depressed patient an effective amount of a compound of claim 1.

12. A method for treating gastrointestinal disorders which comprises administering to a patient with gastrointestinal disorders an effective amount of a compound of claim 1.

13. A composition for the treatment of diabetes or obesity or for lowering triglyceride or cholesterol levels or increasing high density lipoprotein levels or for decreasing gut motility or for reducing neurogenic inflammation or for treating depression or for treating gastrointestinal disorders which comprises an inert carrier and an effective amount of a compound of claim 1.

* * * * *